United States Patent
Cappola et al.

(10) Patent No.: US 11,331,098 B2
(45) Date of Patent: May 17, 2022

(54) SLED DETECTION DEVICE

(71) Applicant: Covidien LP, Mansfield, MA (US)

(72) Inventors: Kenneth Cappola, Monroe, CT (US);
Stanislaw Z. Marczyk, Stratford, CT (US); Russell Pribanic, Roxbury, CT (US); Justin Williams, Southbury, CT (US); John W. Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 125 days.

(21) Appl. No.: 16/837,586

(22) Filed: Apr. 1, 2020

(65) Prior Publication Data
US 2021/0307743 A1 Oct. 7, 2021

(51) Int. Cl.
*A61B 17/068* (2006.01)
*A61B 17/072* (2006.01)
*A61B 90/00* (2016.01)

(52) U.S. Cl.
CPC ........ *A61B 17/0686* (2013.01); *A61B 17/072* (2013.01); *A61B 2017/07257* (2013.01); *A61B 2017/07271* (2013.01); *A61B 2017/07278* (2013.01); *A61B 2017/07285* (2013.01); *A61B 2090/038* (2016.02); *A61B 2090/0807* (2016.02); *A61B 2090/0808* (2016.02); *A61B 2090/0811* (2016.02)

(58) Field of Classification Search
CPC .............. A61B 17/0686; A61B 17/072; A61B 2017/07285; A61B 2017/07278; A61B 2017/07257; A61B 2017/07271; A61B 2090/038

USPC ..................... 227/176.1, 177.1, 175.2–175.4
See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

European Search Report dated Nov. 29, 2021, issued in corresponding EP Appln. No. 21166459, 11 pages.

*Primary Examiner* — Valentin Neacsu

(57) ABSTRACT

A surgical stapling device includes a staple reload and a shipping wedge. In embodiments, the shipping wedge is configured to disable the use of a staple reload if the staple reload does not have an actuation sled. In other embodiments, the actuation sled includes a readable identifier that facilitates confirmation of the presence of an actuation sled within a staple reload from a location externally of the staple reload.

21 Claims, 23 Drawing Sheets

(56) References Cited

U.S. PATENT DOCUMENTS

| | | |
|---|---|---|
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Mien et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Mien et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |

(56) References Cited

U.S. PATENT DOCUMENTS

| | | |
|---|---|---|
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Billner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Mien et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Billner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Billner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |

(56) References Cited

U.S. PATENT DOCUMENTS

| | | |
|---|---|---|
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 * | 6/2006 | Ehrenfels ......... A61B 17/07207 227/175.4 |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 * | 2/2008 | Rethy ................. A61B 17/105 227/175.1 |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |

(56) References Cited

U.S. PATENT DOCUMENTS

| | | | |
|---|---|---|---|
| 7,604,150 | B2 | 10/2009 | Boudreaux |
| 7,604,151 | B2 | 10/2009 | Hess et al. |
| 7,607,557 | B2 | 10/2009 | Shelton, IV et al. |
| 7,611,038 | B2 | 11/2009 | Racenet et al. |
| 7,617,961 | B2 | 11/2009 | Viola |
| 7,624,902 | B2 | 12/2009 | Marczyk et al. |
| 7,624,903 | B2 | 12/2009 | Green et al. |
| 7,631,793 | B2 | 12/2009 | Rethy et al. |
| 7,631,794 | B2 | 12/2009 | Rethy et al. |
| 7,635,073 | B2 | 12/2009 | Heinrich |
| 7,635,074 | B2 | 12/2009 | Olson et al. |
| 7,635,373 | B2 | 12/2009 | Ortiz |
| 7,637,409 | B2 | 12/2009 | Marczyk |
| 7,637,410 | B2 | 12/2009 | Marczyk |
| 7,641,091 | B2 | 1/2010 | Olson et al. |
| 7,641,095 | B2 | 1/2010 | Viola |
| 7,644,848 | B2 | 1/2010 | Swayze et al. |
| 7,648,055 | B2 | 1/2010 | Marczyk |
| 7,651,017 | B2 | 1/2010 | Ortiz et al. |
| 7,654,431 | B2 | 2/2010 | Hueil et al. |
| 7,658,311 | B2 | 2/2010 | Boudreaux |
| 7,658,312 | B2 | 2/2010 | Vidal et al. |
| 7,665,646 | B2 | 2/2010 | Prommersberger |
| 7,665,647 | B2 | 2/2010 | Shelton, IV et al. |
| 7,669,746 | B2 | 3/2010 | Shelton, IV |
| 7,670,334 | B2 | 3/2010 | Hueil et al. |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,678,121 | B1 | 3/2010 | Knodel |
| 7,681,772 | B2 | 3/2010 | Green et al. |
| 7,682,367 | B2 | 3/2010 | Shah et al. |
| 7,682,368 | B1 | 3/2010 | Bombard et al. |
| 7,690,547 | B2 | 4/2010 | Racenet et al. |
| 7,694,865 | B2 | 4/2010 | Scirica |
| 7,699,205 | B2 | 4/2010 | Ivanko |
| 7,703,653 | B2 | 4/2010 | Shah et al. |
| 7,721,931 | B2 | 5/2010 | Shelton, IV et al. |
| 7,721,933 | B2 | 5/2010 | Ehrenfels et al. |
| 7,721,935 | B2 | 5/2010 | Racenet et al. |
| 7,726,537 | B2 | 6/2010 | Olson et al. |
| 7,726,538 | B2 | 6/2010 | Holsten et al. |
| 7,726,539 | B2 | 6/2010 | Holsten et al. |
| 7,731,072 | B2 | 6/2010 | Timm et al. |
| 7,735,703 | B2 | 6/2010 | Morgan et al. |
| 7,740,159 | B2 | 6/2010 | Shelton, IV et al. |
| 7,740,160 | B2 | 6/2010 | Viola |
| 7,743,960 | B2 | 6/2010 | Whitman et al. |
| 7,744,628 | B2 | 6/2010 | Viola |
| 7,753,245 | B2 | 7/2010 | Boudreaux et al. |
| 7,753,248 | B2 | 7/2010 | Viola |
| 7,757,924 | B2 | 7/2010 | Gerbi et al. |
| 7,757,925 | B2 | 7/2010 | Viola et al. |
| 7,762,445 | B2 | 7/2010 | Heinrich et al. |
| 7,766,209 | B2 | 8/2010 | Baxter, III et al. |
| 7,766,210 | B2 | 8/2010 | Shelton, IV et al. |
| 7,766,924 | B1 | 8/2010 | Bombard et al. |
| 7,766,928 | B2 | 8/2010 | Ezzat et al. |
| 7,770,774 | B2 | 8/2010 | Mastri et al. |
| 7,770,775 | B2 | 8/2010 | Shelton, IV et al. |
| 7,776,060 | B2 | 8/2010 | Mooradian et al. |
| 7,780,055 | B2 | 8/2010 | Scirica et al. |
| 7,784,662 | B2 | 8/2010 | Wales et al. |
| 7,789,283 | B2 | 9/2010 | Shah |
| 7,789,889 | B2 | 9/2010 | Zubik et al. |
| 7,793,812 | B2 | 9/2010 | Moore et al. |
| 7,793,814 | B2 | 9/2010 | Racenet et al. |
| 7,794,475 | B2 | 9/2010 | Hess et al. |
| 7,798,385 | B2 | 9/2010 | Boyden et al. |
| 7,798,386 | B2 | 9/2010 | Schall et al. |
| 7,799,039 | B2 | 9/2010 | Shelton, IV et al. |
| 7,810,690 | B2 | 10/2010 | Bilotti et al. |
| 7,810,692 | B2 | 10/2010 | Hall et al. |
| 7,810,693 | B2 | 10/2010 | Broehl et al. |
| 7,815,090 | B2 | 10/2010 | Marczyk |
| 7,815,091 | B2 | 10/2010 | Marczyk |
| 7,815,092 | B2 | 10/2010 | Whitman et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,819,896 | B2 | 10/2010 | Racenet |
| 7,823,760 | B2 | 11/2010 | Zemlok et al. |
| 7,823,761 | B2 | 11/2010 | Boyden et al. |
| 7,824,426 | B2 | 11/2010 | Racenet et al. |
| 7,828,186 | B2 | 11/2010 | Wales |
| 7,828,187 | B2 | 11/2010 | Green et al. |
| 7,828,188 | B2 | 11/2010 | Jankowski |
| 7,828,189 | B2 | 11/2010 | Holsten et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,834,630 | B2 | 11/2010 | Damadian et al. |
| 7,837,079 | B2 | 11/2010 | Holsten et al. |
| 7,837,081 | B2 | 11/2010 | Holsten et al. |
| 7,841,503 | B2 | 11/2010 | Sonnenschein et al. |
| 7,845,533 | B2 | 12/2010 | Marczyk et al. |
| 7,845,534 | B2 | 12/2010 | Viola et al. |
| 7,845,535 | B2 | 12/2010 | Scircia |
| 7,845,537 | B2 | 12/2010 | Shelton, IV et al. |
| 7,845,538 | B2 | 12/2010 | Whitman |
| 7,850,703 | B2 | 12/2010 | Bombard et al. |
| 7,857,183 | B2 | 12/2010 | Shelton, IV |
| 7,857,184 | B2 | 12/2010 | Viola |
| 7,857,185 | B2 | 12/2010 | Swayze et al. |
| 7,857,186 | B2 | 12/2010 | Baxter, III et al. |
| 7,861,906 | B2 | 1/2011 | Doll et al. |
| 7,861,907 | B2 | 1/2011 | Green et al. |
| 7,866,524 | B2 | 1/2011 | Krehel |
| 7,866,525 | B2 | 1/2011 | Scirica |
| 7,866,526 | B2 | 1/2011 | Green et al. |
| 7,866,527 | B2 | 1/2011 | Hall et al. |
| 7,866,528 | B2 | 1/2011 | Olson et al. |
| 7,870,989 | B2 | 1/2011 | Viola et al. |
| 7,886,952 | B2 | 2/2011 | Scirica et al. |
| 7,891,532 | B2 | 2/2011 | Mastri et al. |
| 7,891,533 | B2 | 2/2011 | Green et al. |
| 7,891,534 | B2 | 2/2011 | Wenchell et al. |
| 7,896,214 | B2 | 3/2011 | Farascioni |
| 7,900,805 | B2 | 3/2011 | Shelton, IV et al. |
| 7,901,416 | B2 | 3/2011 | Nolan et al. |
| 7,905,380 | B2 | 3/2011 | Shelton, IV et al. |
| 7,905,381 | B2 | 3/2011 | Baxter, III et al. |
| 7,909,039 | B2 | 3/2011 | Hur |
| 7,909,220 | B2 | 3/2011 | Viola |
| 7,909,221 | B2 | 3/2011 | Viola et al. |
| 7,909,224 | B2 | 3/2011 | Prommersberger |
| 7,913,891 | B2 | 3/2011 | Doll et al. |
| 7,913,893 | B2 | 3/2011 | Mastri et al. |
| 7,914,543 | B2 | 3/2011 | Roth et al. |
| 7,918,230 | B2 | 4/2011 | Whitman et al. |
| 7,922,061 | B2 | 4/2011 | Shelton, IV et al. |
| 7,922,063 | B2 | 4/2011 | Zemlok et al. |
| 7,922,064 | B2 | 4/2011 | Boyden et al. |
| 7,926,691 | B2 | 4/2011 | Viola et al. |
| 7,926,692 | B2 | 4/2011 | Racenet et al. |
| 7,934,628 | B2 | 5/2011 | Wenchell et al. |
| 7,934,630 | B2 | 5/2011 | Shelton, IV et al. |
| 7,934,631 | B2 | 5/2011 | Balbierz et al. |
| 7,942,300 | B2 | 5/2011 | Rethy et al. |
| 7,942,303 | B2 | 5/2011 | Shah |
| 7,950,560 | B2 | 5/2011 | Zemlok et al. |
| 7,950,561 | B2 | 5/2011 | Aranyi |
| 7,950,562 | B2 | 5/2011 | Beardsley et al. |
| 7,954,682 | B2 | 6/2011 | Giordano et al. |
| 7,954,683 | B1 | 6/2011 | Knodel et al. |
| 7,954,684 | B2 | 6/2011 | Boudreaux |
| 7,954,685 | B2 | 6/2011 | Viola |
| 7,954,686 | B2 | 6/2011 | Baxter, III et al. |
| 7,954,687 | B2 | 6/2011 | Zemlok et al. |
| 7,959,051 | B2 | 6/2011 | Smith et al. |
| 7,963,431 | B2 | 6/2011 | Scirica |
| 7,963,432 | B2 | 6/2011 | Knodel et al. |

(56) References Cited

U.S. PATENT DOCUMENTS

| | | | |
|---|---|---|---|
| 7,963,433 | B2 | 6/2011 | Whitman et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,975,894 | B2 | 7/2011 | Boyden et al. |
| 7,980,443 | B2 | 7/2011 | Scheib et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,992,758 | B2 | 8/2011 | Whitman et al. |
| 7,997,468 | B2 | 8/2011 | Farascioni |
| 7,997,469 | B2 | 8/2011 | Olson et al. |
| 8,002,795 | B2 | 8/2011 | Beetel |
| 8,006,885 | B2 | 8/2011 | Marczyk |
| 8,006,887 | B2 | 8/2011 | Marczyk |
| 8,007,505 | B2 | 8/2011 | Weller et al. |
| 8,007,513 | B2 | 8/2011 | Nalagatla et al. |
| 8,011,550 | B2 | 9/2011 | Aranyi et al. |
| 8,011,551 | B2 | 9/2011 | Marczyk et al. |
| 8,011,552 | B2 | 9/2011 | Ivanko |
| 8,011,553 | B2 | 9/2011 | Mastri et al. |
| 8,011,555 | B2 | 9/2011 | Farinelli et al. |
| 8,012,170 | B2 | 9/2011 | Whitman et al. |
| 8,015,976 | B2 | 9/2011 | Shah |
| 8,016,177 | B2 | 9/2011 | Bettuchi et al. |
| 8,016,178 | B2 | 9/2011 | Olson et al. |
| 8,020,742 | B2 | 9/2011 | Marczyk |
| 8,020,743 | B2 | 9/2011 | Shelton, IV |
| 8,028,882 | B2 | 10/2011 | Viola |
| 8,028,883 | B2 | 10/2011 | Stopek |
| 8,028,884 | B2 | 10/2011 | Sniffin et al. |
| 8,033,438 | B2 | 10/2011 | Scirica |
| 8,033,440 | B2 | 10/2011 | Wenchell et al. |
| 8,033,441 | B2 | 10/2011 | Marczyk |
| 8,033,442 | B2 | 10/2011 | Racenet et al. |
| 8,034,077 | B2 | 10/2011 | Smith et al. |
| 8,038,044 | B2 | 10/2011 | Viola |
| 8,038,045 | B2 | 10/2011 | Bettuchi et al. |
| 8,052,024 | B2 | 11/2011 | Viola et al. |
| 8,056,787 | B2 | 11/2011 | Boudreaux et al. |
| 8,056,788 | B2 | 11/2011 | Mastri et al. |
| 8,056,791 | B2 | 11/2011 | Whitman |
| 8,061,577 | B2 | 11/2011 | Racenet et al. |
| 8,066,166 | B2 | 11/2011 | Demmy et al. |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,074,858 | B2 | 12/2011 | Marczyk |
| 8,074,859 | B2 | 12/2011 | Kostrzewski |
| 8,074,862 | B2 | 12/2011 | Shah |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,087,563 | B2 | 1/2012 | Milliman et al. |
| 8,091,753 | B2 | 1/2012 | Viola |
| 8,091,754 | B2 | 1/2012 | Ehrenfels et al. |
| 8,091,756 | B2 | 1/2012 | Viola |
| 8,092,493 | B2 | 1/2012 | Marczyk |
| 8,096,459 | B2 | 1/2012 | Ortiz et al. |
| 8,096,460 | B2 | 1/2012 | Blier et al. |
| 8,100,309 | B2 | 1/2012 | Marczyk |
| 8,100,310 | B2 | 1/2012 | Zemlok |
| 8,102,008 | B2 | 1/2012 | Wells |
| 8,113,406 | B2 | 2/2012 | Holsten et al. |
| 8,113,407 | B2 | 2/2012 | Holsten et al. |
| 8,113,408 | B2 | 2/2012 | Wenchell et al. |
| 8,113,409 | B2 | 2/2012 | Cohen et al. |
| 8,113,410 | B2 | 2/2012 | Hall et al. |
| 8,123,101 | B2 | 2/2012 | Racenet et al. |
| 8,127,975 | B2 | 3/2012 | Olson et al. |
| 8,127,976 | B2 | 3/2012 | Scirica et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,136,713 | B2 | 3/2012 | Hathaway et al. |
| 8,141,762 | B2 | 3/2012 | Bedi et al. |
| 8,152,041 | B2 | 4/2012 | Kostrzewski |
| 8,157,148 | B2 | 4/2012 | Scirica |
| 8,157,150 | B2 | 4/2012 | Viola et al. |
| 8,157,151 | B2 | 4/2012 | Ingmanson et al. |
| 8,157,152 | B2 | 4/2012 | Holsten et al. |
| 8,162,197 | B2 | 4/2012 | Mastri et al. |
| 8,167,185 | B2 | 5/2012 | Shelton, IV et al. |
| 8,167,186 | B2 | 5/2012 | Racenet et al. |
| 8,172,121 | B2 | 5/2012 | Krehel |
| 8,172,124 | B2 | 5/2012 | Shelton, IV et al. |
| 8,181,837 | B2 | 5/2012 | Roy |
| 8,186,555 | B2 | 5/2012 | Shelton, IV et al. |
| 8,186,557 | B2 | 5/2012 | Cohen et al. |
| 8,186,558 | B2 | 5/2012 | Sapienza |
| 8,186,559 | B1 | 5/2012 | Whitman |
| 8,186,560 | B2 | 5/2012 | Hess et al. |
| 8,193,044 | B2 | 6/2012 | Kenneth |
| 8,196,795 | B2 | 6/2012 | Moore et al. |
| 8,196,796 | B2 | 6/2012 | Shelton, IV et al. |
| 8,201,721 | B2 | 6/2012 | Zemlok et al. |
| 8,205,619 | B2 | 6/2012 | Shah et al. |
| 8,205,780 | B2 | 6/2012 | Sorrentino et al. |
| 8,205,781 | B2 | 6/2012 | Baxter, III et al. |
| 8,210,412 | B2 | 7/2012 | Marczyk |
| 8,210,416 | B2 | 7/2012 | Milliman et al. |
| 8,215,532 | B2 | 7/2012 | Marczyk |
| 8,216,236 | B2 | 7/2012 | Heinrich et al. |
| 8,220,688 | B2 | 7/2012 | Laurent et al. |
| 8,220,690 | B2 | 7/2012 | Hess et al. |
| 8,225,979 | B2 * | 7/2012 | Farascioni ....... A61B 17/07207 227/175.2 |
| 8,231,040 | B2 | 7/2012 | Zemlok et al. |
| 8,231,041 | B2 | 7/2012 | Marczyk et al. |
| 8,235,272 | B2 | 8/2012 | Nicholas et al. |
| 8,235,273 | B2 | 8/2012 | Olson et al. |
| 8,235,274 | B2 | 8/2012 | Cappola |
| 8,236,010 | B2 | 8/2012 | Ortiz et al. |
| 8,240,536 | B2 | 8/2012 | Marczyk |
| 8,240,537 | B2 | 8/2012 | Marczyk |
| 8,241,322 | B2 | 8/2012 | Whitman et al. |
| 8,245,897 | B2 | 8/2012 | Tzakis et al. |
| 8,245,898 | B2 | 8/2012 | Smith et al. |
| 8,245,899 | B2 | 8/2012 | Swensgard et al. |
| 8,245,931 | B2 | 8/2012 | Shigeta |
| 8,252,009 | B2 | 8/2012 | Weller et al. |
| 8,256,653 | B2 | 9/2012 | Farascioni |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,267,300 | B2 | 9/2012 | Boudreaux |
| 8,272,551 | B2 | 9/2012 | Knodel et al. |
| 8,272,553 | B2 | 9/2012 | Mastri et al. |
| 8,272,554 | B2 | 9/2012 | Whitman et al. |
| 8,276,594 | B2 | 10/2012 | Shah |
| 8,276,801 | B2 | 10/2012 | Zemlok et al. |
| 8,281,973 | B2 | 10/2012 | Wenchell et al. |
| 8,286,847 | B2 | 10/2012 | Taylor |
| 8,286,848 | B2 | 10/2012 | Wenchell et al. |
| 8,286,850 | B2 | 10/2012 | Viola |
| 8,292,146 | B2 | 10/2012 | Holsten et al. |
| 8,292,147 | B2 | 10/2012 | Viola |
| 8,292,148 | B2 | 10/2012 | Viola |
| 8,292,149 | B2 | 10/2012 | Ivanko |
| 8,292,150 | B2 | 10/2012 | Bryant |
| 8,292,151 | B2 | 10/2012 | Viola |
| 8,292,152 | B2 | 10/2012 | Milliman et al. |
| 8,292,153 | B2 | 10/2012 | Jankowski |
| 8,292,154 | B2 | 10/2012 | Marczyk |
| 8,292,155 | B2 | 10/2012 | Shelton, IV et al. |
| 8,292,156 | B2 | 10/2012 | Kostrzewski |
| 8,292,158 | B2 | 10/2012 | Sapienza |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,044 | B2 | 11/2012 | Viola |
| 8,308,046 | B2 | 11/2012 | Prommersberger |
| 8,308,757 | B2 | 11/2012 | Hillstead et al. |

(56) References Cited

U.S. PATENT DOCUMENTS

| | | | |
|---|---|---|---|
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 * | 3/2013 | Kostrzewski ........ A61B 17/068 227/175.2 |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | Stopek et al. |
| 8,627,994 B2 | 1/2014 | Zemlok et al. |
| 8,628,544 B2 | 1/2014 | Farascioni |

(56) References Cited

U.S. PATENT DOCUMENTS

| | | |
|---|---|---|
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,967,445 B2 * | 3/2015 | Kostrzewski ........ A61B 17/068 227/175.2 |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |

(56) References Cited

U.S. PATENT DOCUMENTS

| | | |
|---|---|---|
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 2004/0007608 A1* | 1/2004 | Ehrenfels ......... A61B 17/07207 227/176.1 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0216055 A1 | 9/2005 | Scirica et al. |
| 2005/0222616 A1* | 10/2005 | Rethy ............... A61B 17/07207 606/215 |
| 2006/0049229 A1 | 3/2006 | Milliman et al. |
| 2006/0151569 A1* | 7/2006 | Ehrenfels ......... A61B 17/07207 227/180.1 |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0167644 A1 | 7/2008 | Shelton et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0051669 A1 | 3/2010 | Milliman |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101066 A1* | 5/2011 | Farascioni ......... A61B 17/07207 227/175.2 |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234894 A1* | 9/2012 | Kostrzewski ..... A61B 17/07207 227/175.2 |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |

(56) References Cited

U.S. PATENT DOCUMENTS

| | | |
|---|---|---|
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0209659 A1* | 7/2014 | Kostrzewski .... A61B 17/07207 227/175.2 |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1* | 9/2014 | Hessler ................ A61B 17/072 227/176.1 |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Meaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0129632 A1* | 5/2015 | Kostrzewski ...... A61B 17/0686 227/175.2 |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0250474 A1 | 9/2015 | Abbott et al. |
| 2015/0297205 A1 | 10/2015 | Zergiebel et al. |
| 2015/0297225 A1 | 10/2015 | Huitema et al. |
| 2015/0316431 A1* | 11/2015 | Collins ............ A61B 17/07207 606/219 |
| 2015/0351765 A1* | 12/2015 | Valentine ............ G06F 11/1448 227/176.1 |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |

(56) References Cited

U.S. PATENT DOCUMENTS

| | | | |
|---|---|---|---|
| 2016/0120542 A1 | 5/2016 | Westling et al. | |
| 2016/0166249 A1 | 6/2016 | Knodel | |
| 2016/0166253 A1 | 6/2016 | Knodel | |
| 2016/0199064 A1 | 7/2016 | Shelton, IV et al. | |
| 2016/0199084 A1 | 7/2016 | Takei | |
| 2016/0206315 A1 | 7/2016 | Olson | |
| 2016/0206336 A1 | 7/2016 | Frushour | |
| 2016/0235494 A1 | 8/2016 | Shelton, IV et al. | |
| 2016/0242773 A1 | 8/2016 | Sadowski et al. | |
| 2016/0242774 A1 | 8/2016 | Ebner | |
| 2016/0242779 A1 | 8/2016 | Aranyi et al. | |
| 2016/0249915 A1 | 9/2016 | Beckman et al. | |
| 2016/0249916 A1 | 9/2016 | Shelton, IV et al. | |
| 2016/0249918 A1 | 9/2016 | Shelton, IV et al. | |
| 2016/0249927 A1 | 9/2016 | Beckman et al. | |
| 2016/0249928 A1* | 9/2016 | Cappola | A61B 90/90 227/176.1 |
| 2016/0249929 A1* | 9/2016 | Cappola | A61B 90/98 227/176.1 |
| 2016/0249945 A1 | 9/2016 | Shelton, IV et al. | |
| 2016/0256071 A1 | 9/2016 | Shelton, IV et al. | |
| 2016/0256152 A1 | 9/2016 | Kostrzewski | |
| 2016/0256154 A1 | 9/2016 | Shelton, IV et al. | |
| 2016/0256160 A1 | 9/2016 | Shelton, IV et al. | |
| 2016/0256161 A1 | 9/2016 | Overmyer et al. | |
| 2016/0256162 A1 | 9/2016 | Shelton, IV et al. | |
| 2016/0256163 A1 | 9/2016 | Shelton, IV et al. | |
| 2016/0256184 A1 | 9/2016 | Shelton, IV et al. | |
| 2016/0256185 A1 | 9/2016 | Shelton, IV et al. | |
| 2016/0256187 A1 | 9/2016 | Shelton, IV et al. | |
| 2016/0262750 A1 | 9/2016 | Hausen et al. | |
| 2016/0270783 A1 | 9/2016 | Yigit et al. | |
| 2016/0270788 A1 | 9/2016 | Czernik | |
| 2016/0278764 A1 | 9/2016 | Shelton, IV et al. | |
| 2016/0278765 A1 | 9/2016 | Shelton, IV et al. | |
| 2016/0278771 A1 | 9/2016 | Shelton, IV et al. | |
| 2016/0278774 A1 | 9/2016 | Shelton, IV et al. | |
| 2016/0278775 A1 | 9/2016 | Shelton, IV et al. | |
| 2016/0278777 A1 | 9/2016 | Shelton, IV et al. | |
| 2016/0278848 A1 | 9/2016 | Boudreaux et al. | |
| 2016/0287250 A1 | 10/2016 | Shelton, IV et al. | |
| 2016/0287251 A1 | 10/2016 | Shelton, IV et al. | |
| 2016/0296216 A1 | 10/2016 | Nicholas et al. | |
| 2016/0296226 A1 | 10/2016 | Kostrzewski | |
| 2016/0302791 A1 | 10/2016 | Schmitt | |
| 2016/0310134 A1 | 10/2016 | Contini et al. | |
| 2016/0324514 A1 | 11/2016 | Srinivas et al. | |
| 2016/0324518 A1 | 11/2016 | Nicholas et al. | |
| 2016/0338703 A1 | 11/2016 | Scirica et al. | |
| 2016/0345971 A1 | 12/2016 | Bucciaglia et al. | |
| 2016/0345973 A1 | 12/2016 | Marczyk et al. | |
| 2016/0354176 A1 | 12/2016 | Schmitt | |
| 2016/0374678 A1 | 12/2016 | Becerra et al. | |
| 2017/0000483 A1 | 1/2017 | Motai et al. | |
| 2017/0020525 A1 | 1/2017 | Shah | |
| 2018/0344315 A1* | 12/2018 | Calderoni | A61B 90/90 |
| 2019/0046201 A1* | 2/2019 | Labhasetwar | A61B 17/128 |
| 2019/0059896 A1* | 2/2019 | Beardsley | A61B 17/064 |
| 2019/0159777 A1* | 5/2019 | Ehrenfels | A61B 17/07207 |
| 2019/0200971 A1 | 7/2019 | Whitfield et al. | |
| 2019/0336126 A1* | 11/2019 | Williams | A61B 50/30 |
| 2020/0129177 A1* | 4/2020 | Cappola | A61B 17/07207 |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2907456 A1 | 8/2015 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 20150191887 A1 | 12/2015 |

* cited by examiner

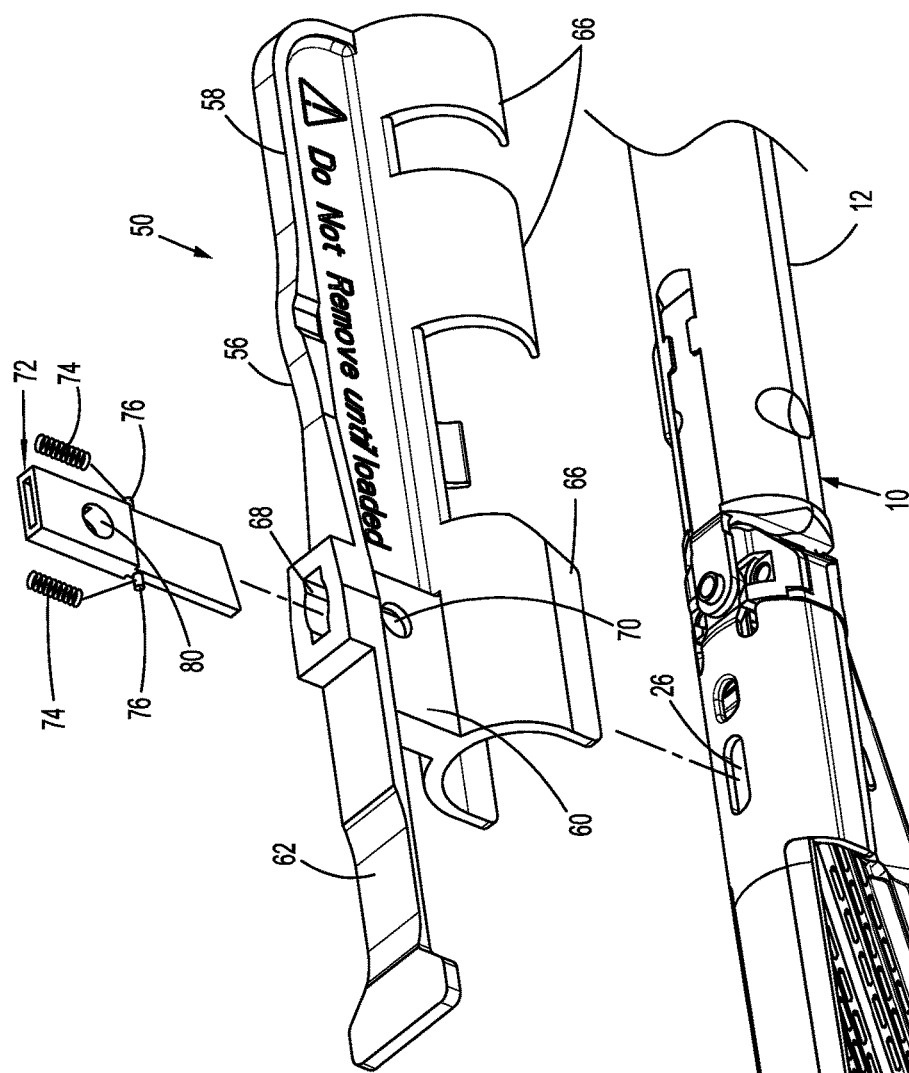
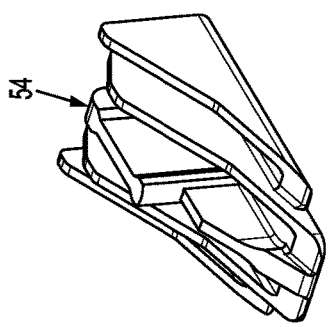
FIG. 2A
FIG. 2

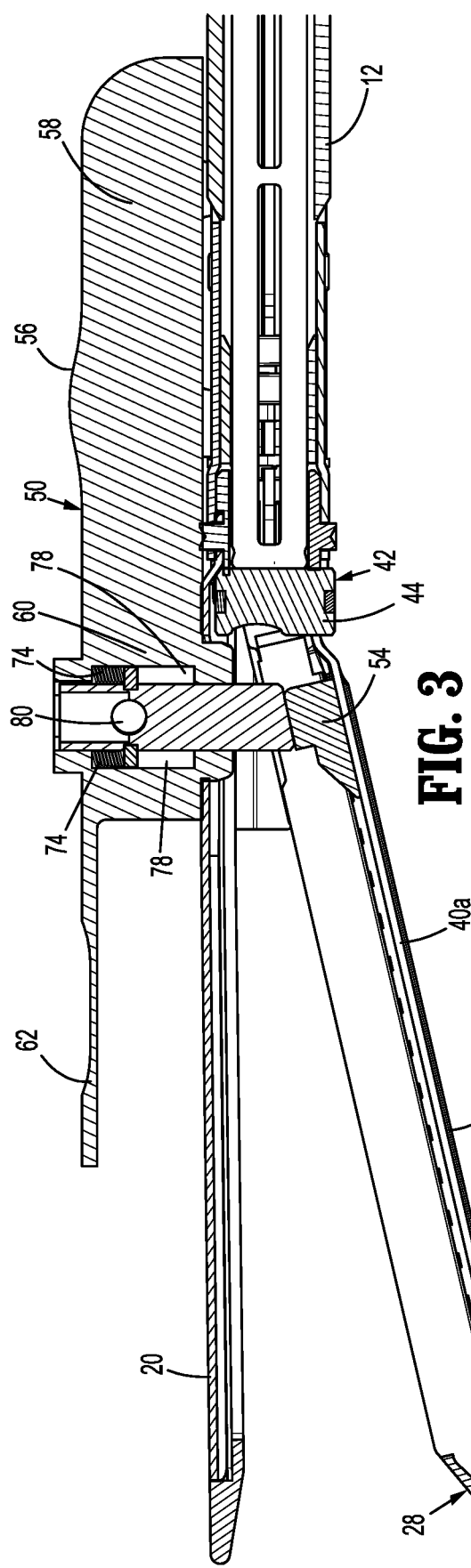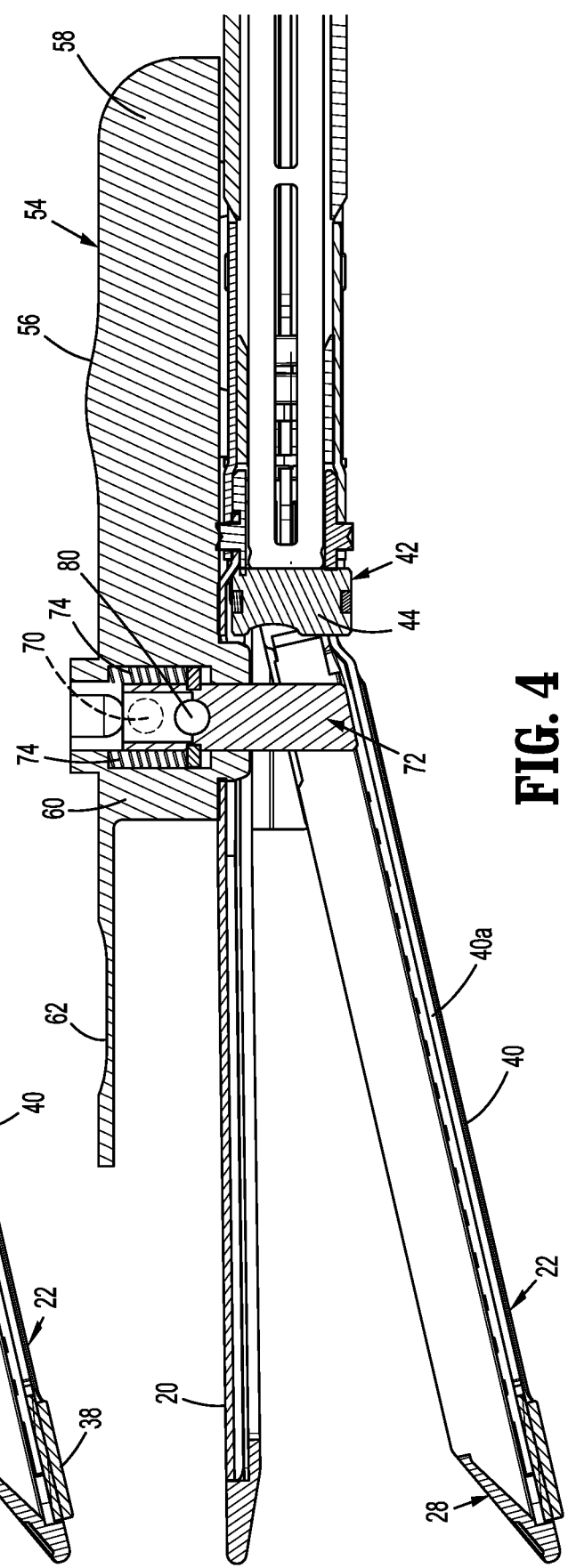

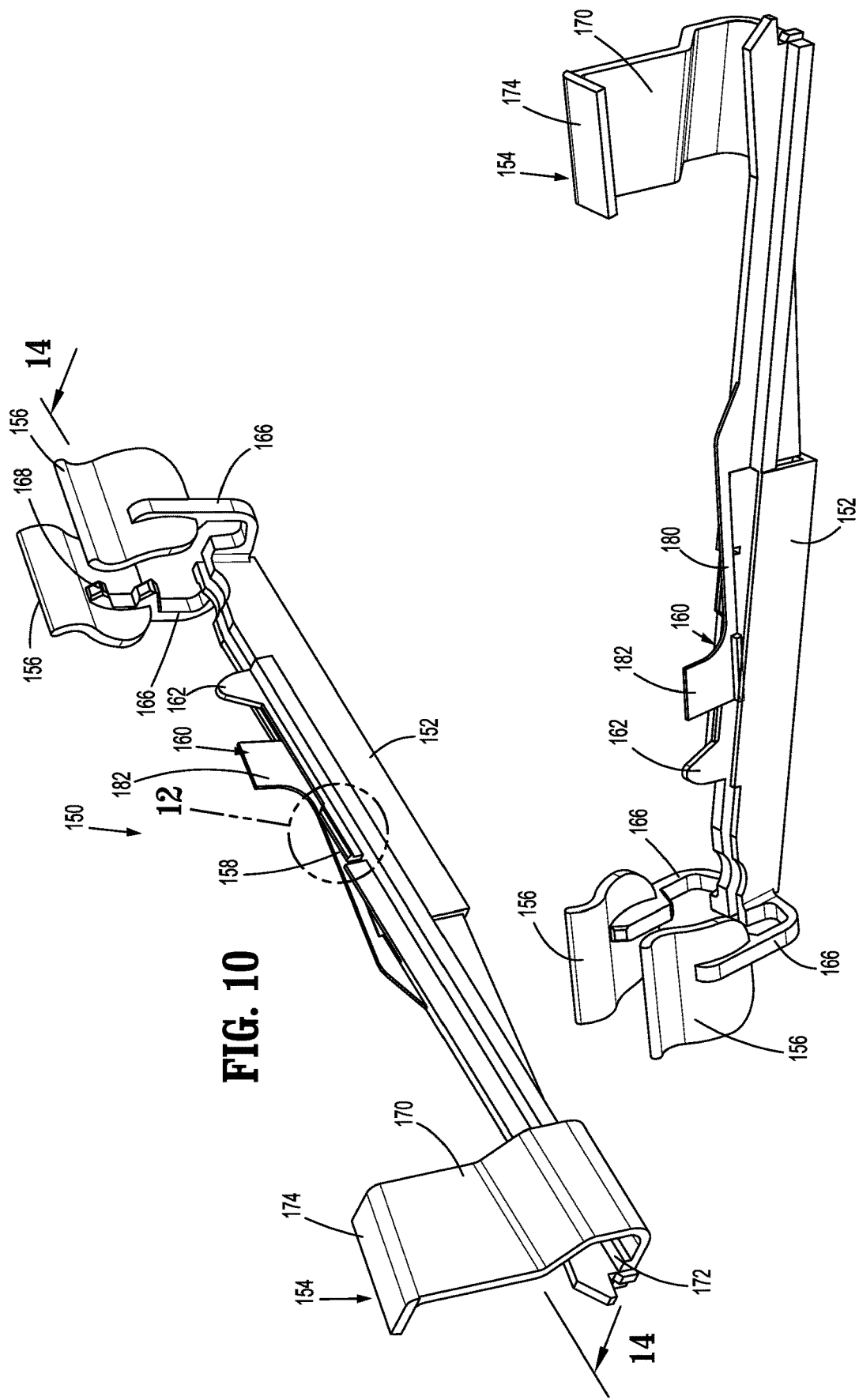

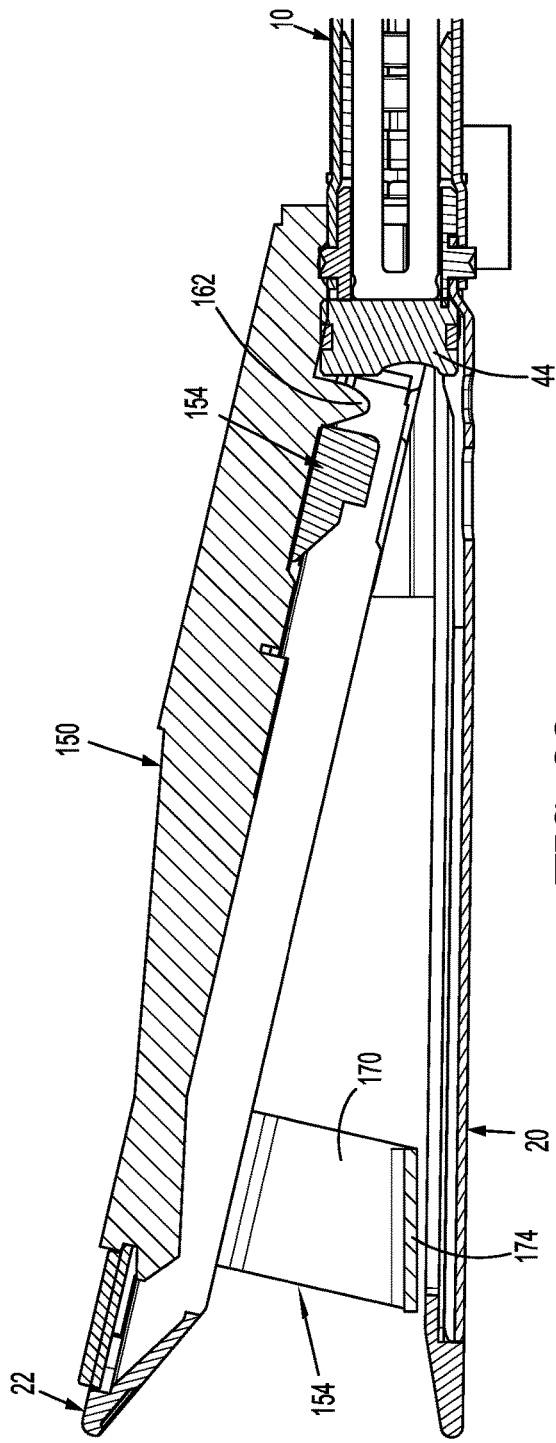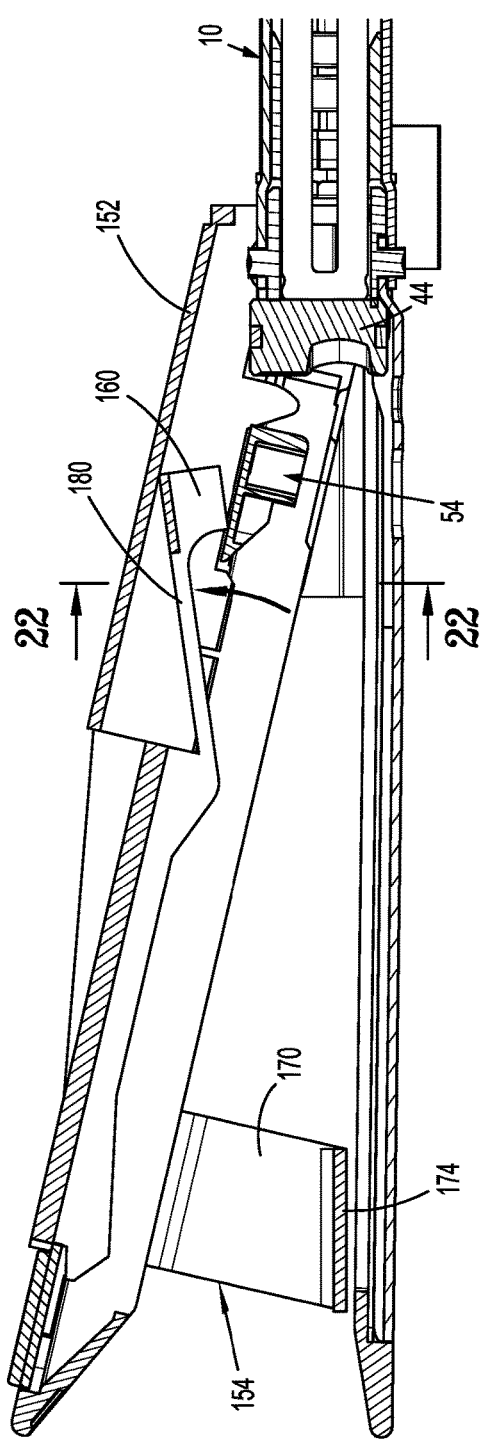

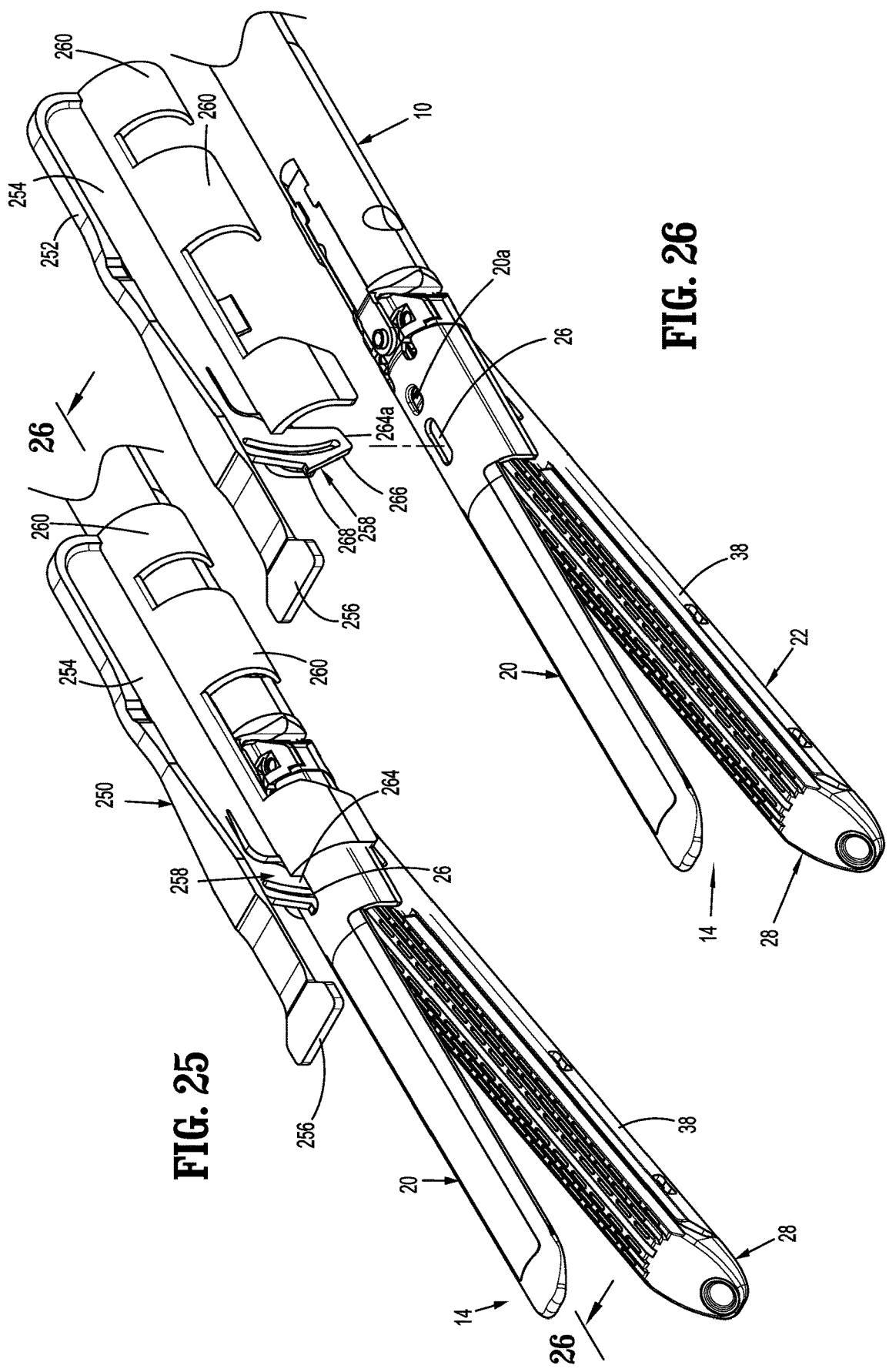

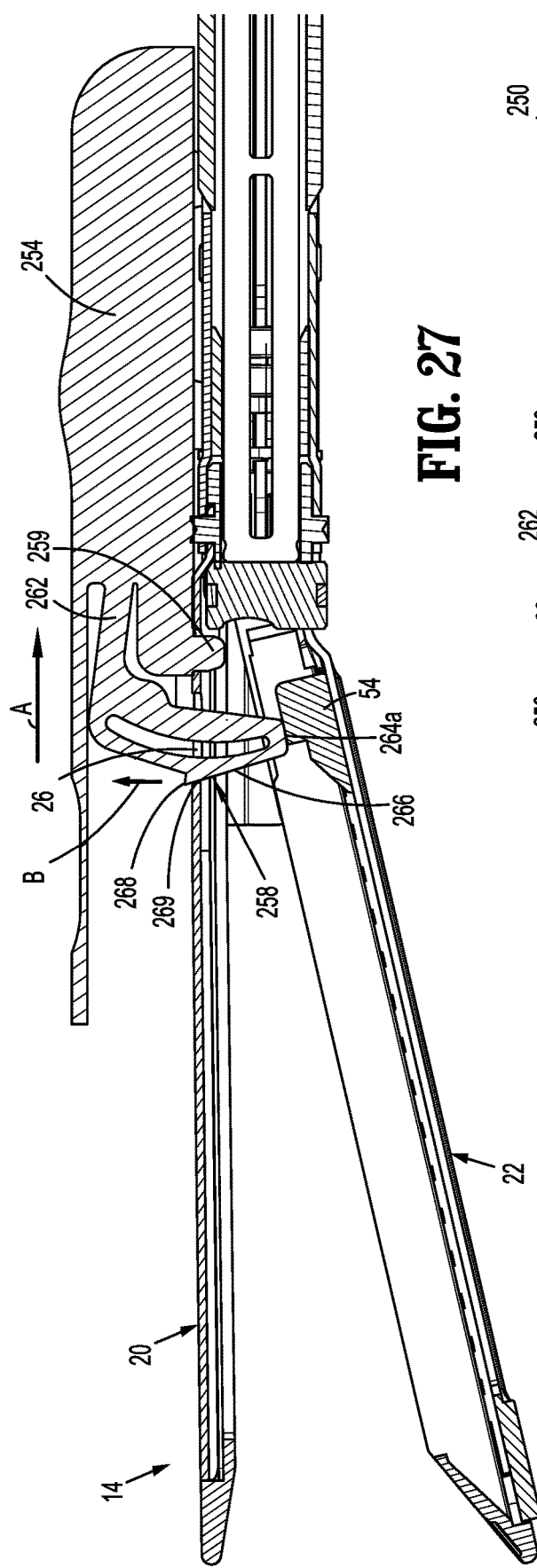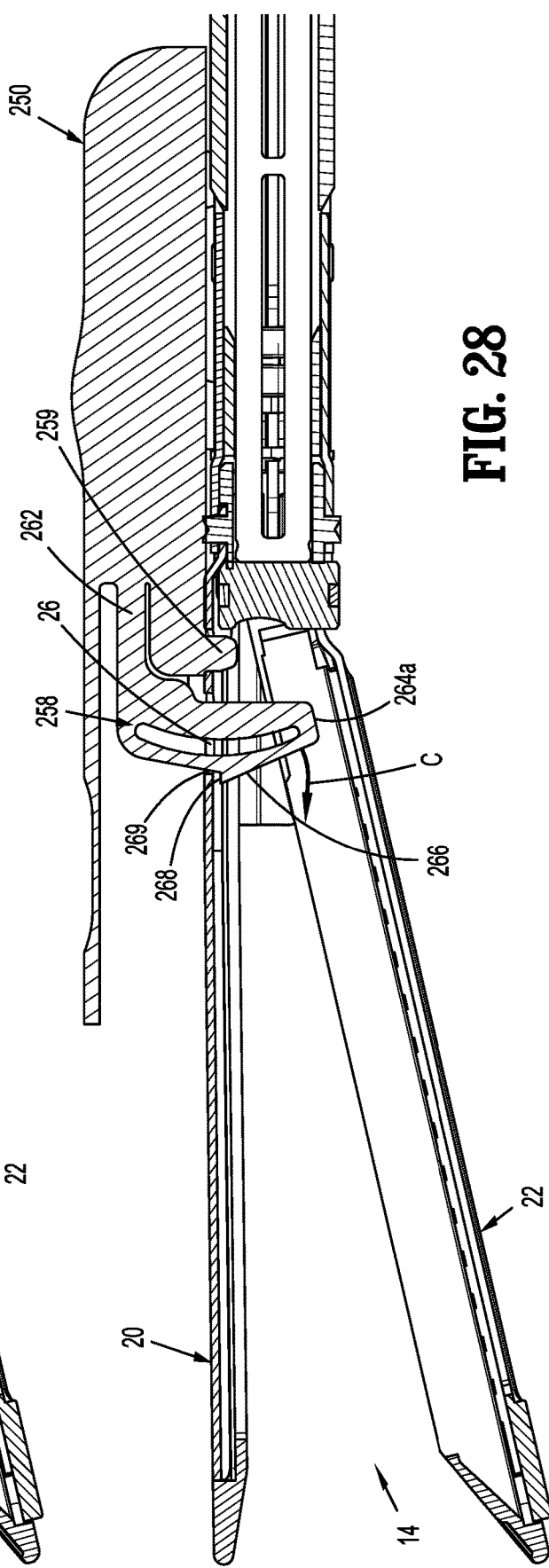

SLED DETECTION DEVICE

FIELD

The disclosure is directed to surgical stapling devices and, more particularly, to devices for detecting the presence of an actuation sled in a tool assembly of a surgical stapling device.

BACKGROUND

Surgical stapling devices for simultaneously stapling and cutting tissue are known in the art and are available in a variety of open and endoscopic configurations including linear, circular, and curved. Typically, linear surgical stapling devices that are configured for endoscopic use include a staple cartridge that includes a knife bar for cutting tissue and a sled that is movable through the staple cartridge to eject staples from the staple cartridge. In some devices, the sled is positioned to be engaged and advanced through the staple cartridge by the knife bar.

When an actuation sled is not present in the tool assembly, advancement of the knife bar through the staple cartridge of the stapling device cuts body tissue but does not affect stapling of the body tissue. This may have serious consequences for the patient. Although multiple checks are provided during a manufacturing process to confirm the presence of an actuation sled within a tool assembly of the stapling device, a continuing need exists in the art for a mechanism that can more accurately detect the absence of an actuation sled within the tool assembly and/or prevent the use of the tool assembly that does not include a sled assembly.

SUMMARY

One aspect of the disclosure is directed to a surgical stapling device and package assembly including a stapling device, a shipping wedge, and a package. The stapling device includes a tool assembly including an anvil, a cartridge assembly, and a knife bar. The cartridge assembly is coupled to the anvil such that the tool assembly is movable between an open position and a clamped position. The cartridge assembly includes an actuation sled, and the knife bar and the actuation sled are movable through the tool assembly to eject staples from the staple cartridge. The shipping wedge is releasably coupled to the stapling device and includes a body and a detection member supported on the body for movement between first and second positions. The detection member is positioned to extend into the tool assembly and engage the actuation sled when the shipping wedge is coupled to the stapling device, wherein engagement of the detection member with the actuation sled moves the detection member from the second position to the first position. The package defines a cavity for receiving the stapling device and shipping wedge when the shipping wedge is coupled to the stapling device, the cavity being configured to receive the stapling device and shipping wedge within the cavity when the detection member is in the first position and to prevent reception of the stapling device and shipping wedge within the cavity when the detection member is in the second position.

In embodiments, the shipping wedge includes a biasing assembly that is positioned to bias the detection member towards the second position.

In some embodiments, the shipping wedge includes a housing portion that defines a channel and a transverse bore that extends through the housing portion into the channel, and the detection member defines a detection member bore that is aligned with the transverse bore when the detection member is in the first position and is misaligned with the transverse bore when the detection member is in the second position.

In certain embodiments, the package includes a post that positioned within the cavity and is configured to pass through the transverse bore of the housing portion of the shipping wedge and the detection member bore when the detection member is in the first position and to prevent placement of the stapling device and shipping wedge into the cavity when the detection member is in the second position.

In embodiments, the shipping wedge includes a plurality of resilient clip members that are configured to releasably engage the stapling device to secure the shipping wedge to the stapling device.

In some embodiments, the anvil includes a through bore and the detection member extends through the through bore and into the cartridge assembly when the shipping wedge is secured to the stapling device.

In certain embodiments, the shipping wedge includes a housing portion that defines a channel having first and second ends, and the detection member extends from the first end of the channel when the detection member is in the first position and extends from the second end of the channel when the detection member is in the second position.

In embodiments, the cavity of the package is configured to receive the stapling device and the shipping wedge when the detection member is in the first position and to prevent placement of the stapling device and the shipping wedge into the cavity when the detection member is in the second position.

Another aspect of the disclosure is directed to a surgical stapling device including a tool assembly, a body portion, and a shipping wedge. The tool assembly includes an anvil and a cartridge assembly coupled to the anvil such that the tool assembly is movable between an open position and a clamped position. The body portion supports a drive assembly including a knife bar. The cartridge assembly includes a channel and a staple cartridge positioned within the channel. The channel includes a wall defining a longitudinal slot that facilitates passage of the knife bar through the cartridge assembly. The staple cartridge includes an actuation sled, and the knife bar and the actuation sled are movable through the tool assembly from a retracted position to an advanced position to eject staples from the staple cartridge. The shipping wedge is releasably coupled to the stapling device and includes a body portion, a retaining member, and a detection member. The retaining member extends through the longitudinal slot in the channel of the cartridge assembly to secure the shipping wedge to the stapling device. The retaining member is movable within the longitudinal slot of the channel from a locked position in which the retaining member is locked within the longitudinal slot to an unlocked position in which the retaining member is removable from the longitudinal slot. The detection member is supported on the body for movement between first and second positions and extends into the tool assembly into engagement with the actuation sled when the shipping wedge is coupled to the stapling device. Engagement of the detection member with the actuation sled moves the detection member from the second position to the first position, wherein in the second position, the detection member is positioned to prevent movement of the retaining member from the locked position to the unlocked position.

In embodiments, the retaining member includes a vertical strut and a transverse shoulder, wherein the vertical strut extends through the longitudinal slot of the channel and the transverse shoulder engages the wall of the channel when the retaining member is in the locked position to obstruct removal of the shipping wedge from the stapling device.

In some embodiments, the vertical strut is movable within the longitudinal slot of the channel to move the retaining member between the locked position and the unlocked position.

In certain embodiments, the detection member is supported on a resilient arm that is positioned within the longitudinal slot of the channel adjacent to the vertical strut of the retaining member when the detection member is in the second position to prevent movement of the retaining member from the locked position to the unlocked position.

In embodiments, the shipping wedge includes a plurality of resilient clip members that are configured to releasably engage the stapling device to secure the shipping wedge to the surgical stapling device.

In some embodiments, the stapling device includes a mounting assembly that is secured to the tool assembly, wherein the mounting assembly pivotably couples the tool assembly to the body portion of the stapling device such that the tool assembly can pivot in relation to the body portion.

In certain embodiments, each of the plurality of clip members includes a finger that is received between the mounting assembly and the body portion of the stapling device when the shipping wedge is coupled to the tool assembly to obstruct pivotable movement of the tool assembly in relation to the body portion of the surgical stapling device.

In embodiments, the shipping wedge includes a stop member that is positioned to extend through the longitudinal slot of the channel to obstruct movement of the knife from the retracted position towards the advanced position when the shipping wedge is coupled to the stapling device.

In some embodiments, the shipping wedge includes a stop member that extends outwardly from the body portion and is positioned to engage the anvil when the shipping wedge is coupled to the tool assembly to retain the tool assembly in the open position.

Another aspect of the disclosure is directed to a surgical stapling device including a tool assembly, a body portion, and a shipping wedge. The tool assembly extends from the body portion and includes an anvil and a cartridge assembly coupled to the anvil such that the tool assembly is movable between an open position and a clamped position. The anvil defines a through bore. The body portion supports a drive assembly including a knife bar. The cartridge assembly includes a staple cartridge having an actuation sled, and the knife bar and the actuation sled are movable through the tool assembly to eject staples from the staple cartridge. The shipping wedge is releasably coupled to the stapling device and includes a body portion and a detection member supported on the body portion. The detection member is supported on a resilient arm that extends from the body portion and includes a locking member. The detection member is positioned to extend through the through bore of the anvil and into the tool assembly into engagement with the actuation sled when the shipping wedge is coupled to the stapling device. The detection member is movable between a first position in which the locking member is positioned externally of the through bore of the anvil when the shipping wedge is coupled to the stapling device to a second position in which the locking member is positioned through the through bore of the anvil when the shipping wedge is coupled to the stapling device to lock the shipping wedge onto the stapling device, wherein engagement between the detection member and the actuation sled during coupling of the shipping wedge to the stapling device moves the detection member from the second position to the first position.

In some embodiments, the locking member includes a stepped shoulder formed on the detection member.

In certain embodiments, the detection member includes a cam surface and the stepped shoulder is positioned along the cam surface.

In embodiments, the cam surface is positioned to engage a portion of the anvil defining the through bore to resiliently deform the detection member such that when the locking member passes through the through bore, the stepped shoulder snaps into engagement with the portion of the anvil defining the through bore to lock the shipping wedge onto the stapling device.

In some embodiments, engagement between the detection member and the actuation sled deforms the resilient arm to prevent entry of the locking member into the tool assembly.

Another aspect of the disclosure is directed to a surgical stapling device including a tool assembly and a body portion. The tool assembly extends from the body portion and includes an anvil and a cartridge assembly coupled to the anvil such that the tool assembly is movable between an open position and a clamped position. The body portion supports a drive assembly including a knife bar. The cartridge assembly includes a channel and a staple cartridge positioned within the channel having an actuation sled. The channel includes a wall defining a longitudinal slot that facilitates passage of the knife bar through the cartridge assembly, the knife bar and the actuation sled being movable through the tool assembly from a retracted position to an advanced position to eject staples from the staple cartridge. A locking member is supported on the channel that has a finger positioned distally of the knife bar. The finger is movable from a first position blocking distal movement of the knife bar to a second position removed from a path of the knife bar. The actuation sled is positioned between the finger of the locking member and the knife bar and includes an engagement member that is positioned to engage the finger of the resilient locking member when the knife bar is moved from the retracted position towards the advanced position to move the finger from the first position to the second position.

In embodiments, the locking member is formed of a resilient material and the finger is biased towards the first position.

In some embodiments, the engagement member of the actuation sled includes a ramp member that is movable into engagement with the finger to bias the finger to the second position.

Another aspect of the disclosure is directed to a tool assembly including a body portion, an anvil, and a cartridge assembly. The cartridge assembly is coupled to the anvil such that the tool assembly is movable between an open position and a clamped position. The body portion supports a drive assembly including a knife bar. The cartridge assembly includes a channel and an actuation sled. The channel has a wall defining a longitudinal slot that facilitates passage of the knife bar through the cartridge assembly such that the knife bar and the actuation sled are movable through the tool assembly to eject staples from the staple cartridge. The actuation sled supports a readable identifier that can be read to facilitate confirmation of the presence of an actuation sled within the tool assembly from a position externally of the tool assembly.

In embodiments, the readable identifier is a barcode.

In some embodiments, the readable identifier is an RFID.

In certain embodiments, the readable identifier is visible through the longitudinal slot of the channel of the cartridge assembly.

Another aspect of the disclosure is directed to a surgical stapling device including a tool assembly, a body portion, and a shipping wedge. The tool assembly extends from the body portion and includes an anvil defining a through bore and a cartridge assembly that is coupled to the anvil such that the tool assembly is movable between an open position and a clamped position. The body portion supports a drive assembly that includes a knife bar. The cartridge assembly includes a staple cartridge having an actuation sled. The knife bar and the actuation sled are movable through the tool assembly to eject staples from the staple cartridge. The shipping wedge is releasably coupled to the stapling device and includes a body portion and a detection member supported on the body portion. The detection member includes a locking member having a locking surface. The detection member is positioned to extend through the through bore of the anvil and into the tool assembly into engagement with the actuation sled when the shipping wedge is coupled to the stapling device. The detection member is movable between a first position in which the locking surface of the locking member does not pass through the through bore of the anvil when the shipping wedge is coupled to the stapling device to a second position in which the locking member passes through the through bore of the anvil when the shipping wedge is coupled to the stapling device to lock the shipping wedge onto the stapling device. The detection member is positioned to engage the actuation sled during coupling of the shipping wedge to the stapling device to move the detection member from the second position to the first position.

Another aspect of the disclosure is directed to a shipping wedge including a body portion and a detection member supported on the body portion. The detection member includes a locking member having a locking surface. The detection member is positioned to extend through a bore of a tool assembly into engagement with an inner component of the tool assembly when the shipping wedge is coupled to the tool assembly. The detection member is movable between a first position in which the locking surface of the locking member does not pass through the through bore of the tool assembly when the shipping wedge is coupled to the tool assembly to a second position in which the locking member is positioned to pass through the through bore of the tool assembly when the shipping wedge is coupled to the tool assembly to lock the shipping wedge onto the tool assembly. The detection member is positioned to engage the inner component of the tool assembly during coupling of the shipping wedge to the tool assembly to move the detection member from the second position to the first position.

In embodiments, the detection member is supported on a resilient arm that extends from the body portion of the shipping wedge.

In some embodiments, the locking surface of the locking member includes a stepped shoulder formed on the detection member.

In certain embodiments, the detection member includes a cam surface and the stepped shoulder is positioned along the cam surface.

In embodiments, the cam surface is positioned to engage a portion of the anvil defining the through bore to resiliently deform the detection member such that when the locking member passes through the through bore, the stepped shoulder snaps into engagement with the portion of the anvil defining the through bore to lock the shipping wedge onto the anvil.

In some embodiments, engagement between the detection member and the actuation sled deforms the resilient arm to prevent entry of the locking member into the tool assembly.

In certain embodiments, the detection member is coupled to the body portion of the shipping wedge by a pivot member.

In embodiments, the detection member includes an upper body portion and a lower body portion that supports the locking member.

In some embodiments, the locking member includes a resilient finger that extends towards the upper body portion and transversely outwardly from the lower body portion of the locking member.

In certain embodiments, the lower body portion of the detection member includes an engagement surface that is positioned to engage the actuation sled when the shipping wedge is attached to the tool assembly, wherein the engagement surface is angled towards the upper body portion in a proximal direction.

BRIEF DESCRIPTION OF THE DRAWINGS

Various embodiments of the disclosed device for detecting the presence of an actuation sled within a tool assembly of a surgical stapling device are described herein below with reference to the drawings, wherein:

FIG. 2 is a side perspective view of the staple reload and shipping wedge shown in FIG. 1 with parts separated;

FIG. 2A is a side perspective view of an actuation sled of the staple reload shown in FIG. 2;

FIG. 3 is a cross-sectional view of the staple reload shown in FIG. 2 with an actuation sled positioned within the tool assembly of the staple reload;

FIG. 4 is a cross-sectional view of the staple reload shown in FIG. 2 without an actuation sled positioned within the tool assembly of the staple reload;

FIG. 10 is a side perspective view from one side of another exemplary embodiment of the disclosed shipping wedge;

FIG. 11 is a perspective view from the other side of the shipping wedge shown in FIG. 10;

FIG. 20 is a cross-sectional view taken along section line 20-20 of FIG. 17;

FIG. 21 is a cross-sectional view taken along section line 21-21 of FIG. 17 illustrating the interaction between the actuation sled and a wedge member of the shipping wedge;

FIG. 25 is a side perspective view of another exemplary embodiment of a staple reload and a shipping wedge for detecting the presence of an actuation sled within a tool assembly of the staple reload with the tool assembly in an open position;

FIG. 26 is a side perspective view of the staple reload and the shipping wedge shown in FIG. 25 with parts separated;

FIG. 27 is a cross-sectional view taken along section line 27-27 of FIG. 25 with an actuation sled present in the staple cartridge of the tool assembly of the staple reload;

FIG. 28 is a cross-sectional view taken along section line 27-27 of FIG. 25 with an actuation sled missing from the staple cartridge of the tool assembly of the staple reload;

DETAILED DESCRIPTION

Figure 1:
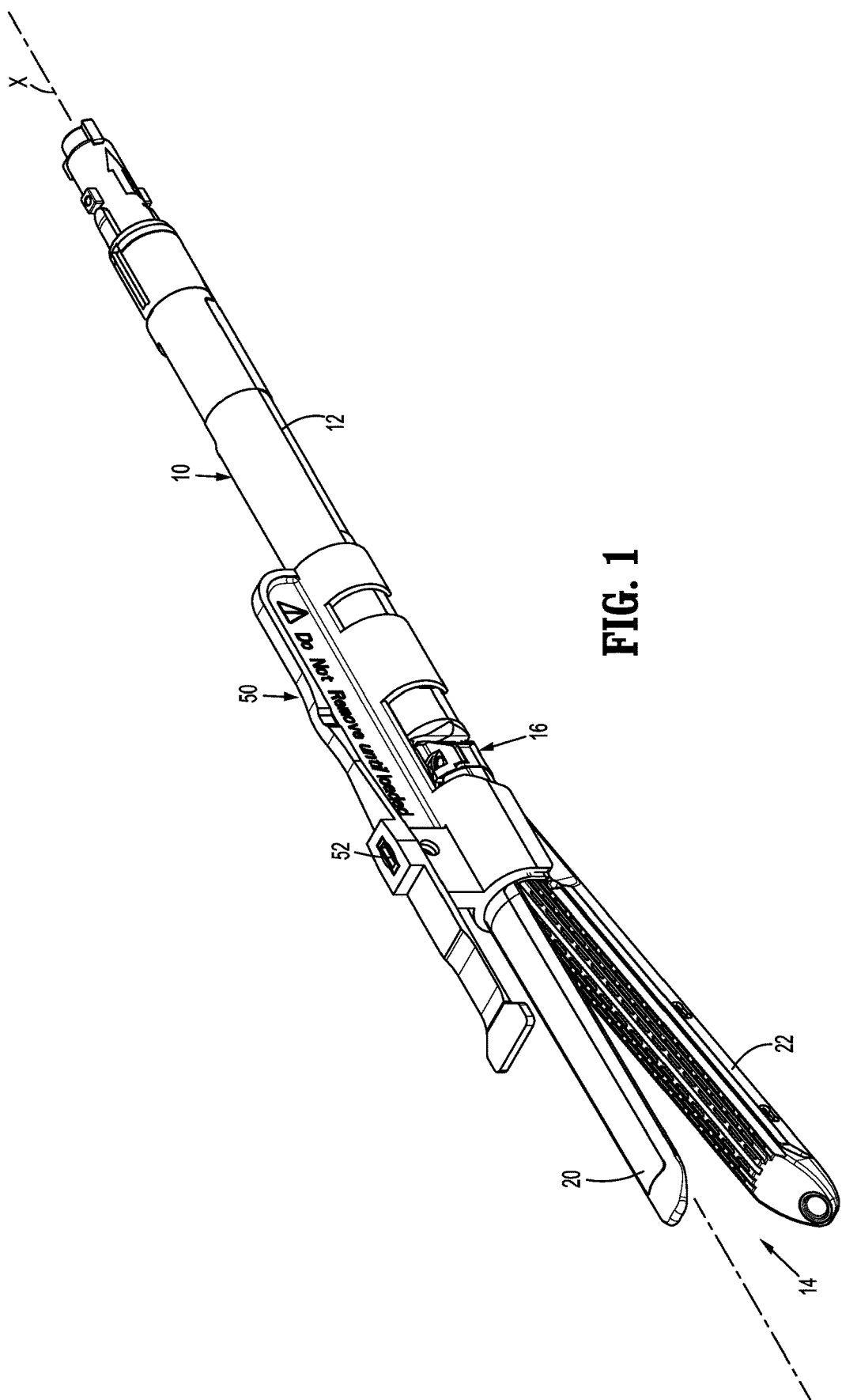
FIG. 1 is a side perspective view of an exemplary embodiment of a staple reload and shipping wedge for detecting the presence of an actuation sled within a tool assembly of the staple reload with the tool assembly in an open position.

The disclosed devices for detecting the presence of an actuation sled within a tool assembly of a surgical stapling device and their associated methods of use will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

FIGS. 1-5 illustrate an exemplary embodiment of a shipping wedge 50 including a device 52 for detecting the presence of an actuation sled 54 (FIG. 2A) in association with a surgical stapling device. As illustrated herein, the surgical stapling device 10 is shown generally as a staple reload 10 that includes a proximal body portion 12 that can be releasably coupled to a handle assembly (not shown) of a surgical stapling device. Alternately, the surgical stapling device or staple reload 10 can be configured to be coupled to a robotic system or can be fixedly coupled to a handle assembly for selective actuation. For a more detailed description of a surgical stapling device including exemplary embodiments of the handle assembly and the staple reload, see, e.g., U.S. Pat. No. 7,565,993 ("the '993 patent") and U.S. Pat. No. 8,931,683 ("the '683 patent"), which are incorporated herein in their entirety FIGS. 1 and 2 illustrate the staple reload 10 and the shipping wedge 50. The staple reload 10 includes the proximal body portion 12 which defines a longitudinal axis "X", a tool assembly 14, and a mounting assembly 16. The mounting assembly 16 has a first end that is secured to the tool assembly 14 and a second end that is pivotally secured to the proximal body portion 14 such that the tool assembly 14 can pivot between a position aligned with the longitudinal axis "X" of the proximal body portion 12 to positions that define an acute angle with the longitudinal axis "X". For a more detailed description of exemplary embodiments of a stapling device including a staple reload with a pivotable tool assembly, see, e.g., the '993 and '683 patents.

Referring also to FIGS. 3 and 4, the tool assembly 14 includes an anvil 20 and a cartridge assembly 22. The anvil 20 is coupled to the cartridge assembly 22 by a pivot member (not shown) such that the cartridge assembly 22 can pivot in relation to the anvil 20 between open and clamped positions. The anvil 20 includes a proximal end portion 24 that defines a through bore 26 (FIG. 2) that extends into the tool assembly 14 and communicates with the cartridge assembly 22.

The cartridge assembly 22 includes a staple cartridge 28 having a body 30 that defines a plurality of rows of staple receiving slots 32 and a knife slot 36. The staple receiving slots 32 are positioned on opposite sides of the knife slot 36 and receive a plurality of staples (not shown). The cartridge assembly 22 also includes a channel 38 that is positioned and dimensioned to receive the staple cartridge 28. The channel 38 includes a bottom wall 40 that defines a knife slot 40a (FIG. 3) that is longitudinally aligned with the knife slot 36 in the staple cartridge 28. In embodiments, the channel 38 is configured to releasably receive the staple cartridge 28 to facilitate replacement of the staple cartridge 28 after each use.

The staple reload 10 includes a drive assembly 42 (FIG. 3) that is movable from a retracted position to an advanced position to move the anvil 20 and the cartridge assembly 22 between the open and clamped positions. The drive assembly 42 includes a knife bar 44 that is positioned proximally of the actuation sled 54 and is configured to move through the longitudinal slots 36, 40a in the staple cartridge 28 and the channel 38 to cut tissue clamped between the anvil and the cartridge assembly. For a detailed description of an exemplary drive assembly, see, e.g., the '993 and '683 patents.

The shipping wedge 50 includes a body 56 that is formed of a resilient material and includes a grip portion 58, a housing portion 60, an extension 62, and a plurality of clip members 66 that extend from the grip portion 58 and/or the housing portion 60. The extension 62 extends distally from the housing portion 60 and may be grasped to assist in removal of the shipping wedge 50 from the staple reload 10. The clip members 66 are configured be snap-fit over the staple reload 10 to secure the shipping wedge 50 to the staple reload 10. In embodiments, the clip members 66 are semi-circular in shape and can flex outwardly to receive the staple reload 10.

The housing portion 60 of the shipping wedge 50 defines a channel 68 that is aligned with the through bore 26 in the anvil 20 when the shipping wedge 50 is coupled to the staple reload 10 and receives the detection device 52. The housing portion 60 of the shipping wedge 50 also defines a bore 70 that intersects and defines an axis that is transverse to the longitudinal axis of the channel 68.

The detection device 52 includes a detection member or slide 72 and a biasing member 74. The slide 72 is received within the channel 68 of the housing portion 60 and includes an abutment, e.g., flexible detent 76, that is received in a groove 78 formed in the housing portion 60 to limit movement of the slide 72 within the channel 68 between a first position (FIG. 3) and a second position (FIG. 4). The slide 72 also defines a bore 80 that is aligned with the bore 70 in the housing portion 60 of the shipping wedge 54 when the slide 72 is in the first position. The biasing member 74 is received within the groove 78 of the housing portion 60 and abuts detents 76 on the slide 72 to urge the slide 72 towards the second position.

The actuation sled 54 is received within the tool assembly 14 and is movable through the staple cartridge 28 in response to movement of the drive assembly 42 between retracted and advanced positions to eject staples (not shown) from the staple cartridge 28. See, e.g., the '993 and '683 patents. When the actuation sled 54 is in its retracted position, the actuation sled 54 is aligned with the through bore 26 in the anvil 20. As such, when the shipping wedge 50 is attached to the staple reload 10, the slide 72 passes through the through bore 26 into the tool assembly 14 and into engagement with the actuation sled 54 when an actuation sled 54 is present within the tool assembly 14. When the slide 72 engages the actuation sled 54 as the shipping wedge 50 is clipped onto the staple reload 10, the slide 72 is moved from its second position to its first position (FIG. 3) and the biasing member 74 is compressed. As described above, in the first position of the slide member 72 (FIG. 3), the bore 70 (FIG. 2) in the housing portion 60 of the shipping wedge 50 is aligned with the bore 80 in the slide 72. However, when an actuation sled 54 is not present in the tool assembly 14, the slide 72 remains in the second position (FIG. 4) as the shipping wedge 50 is coupled to the staple reload 10. When the slide 72 is in the second position, the bore 70 in the housing portion 60 of the shipping wedge 50 is misaligned with the bore 80 in the slide 72.

Figure 5:
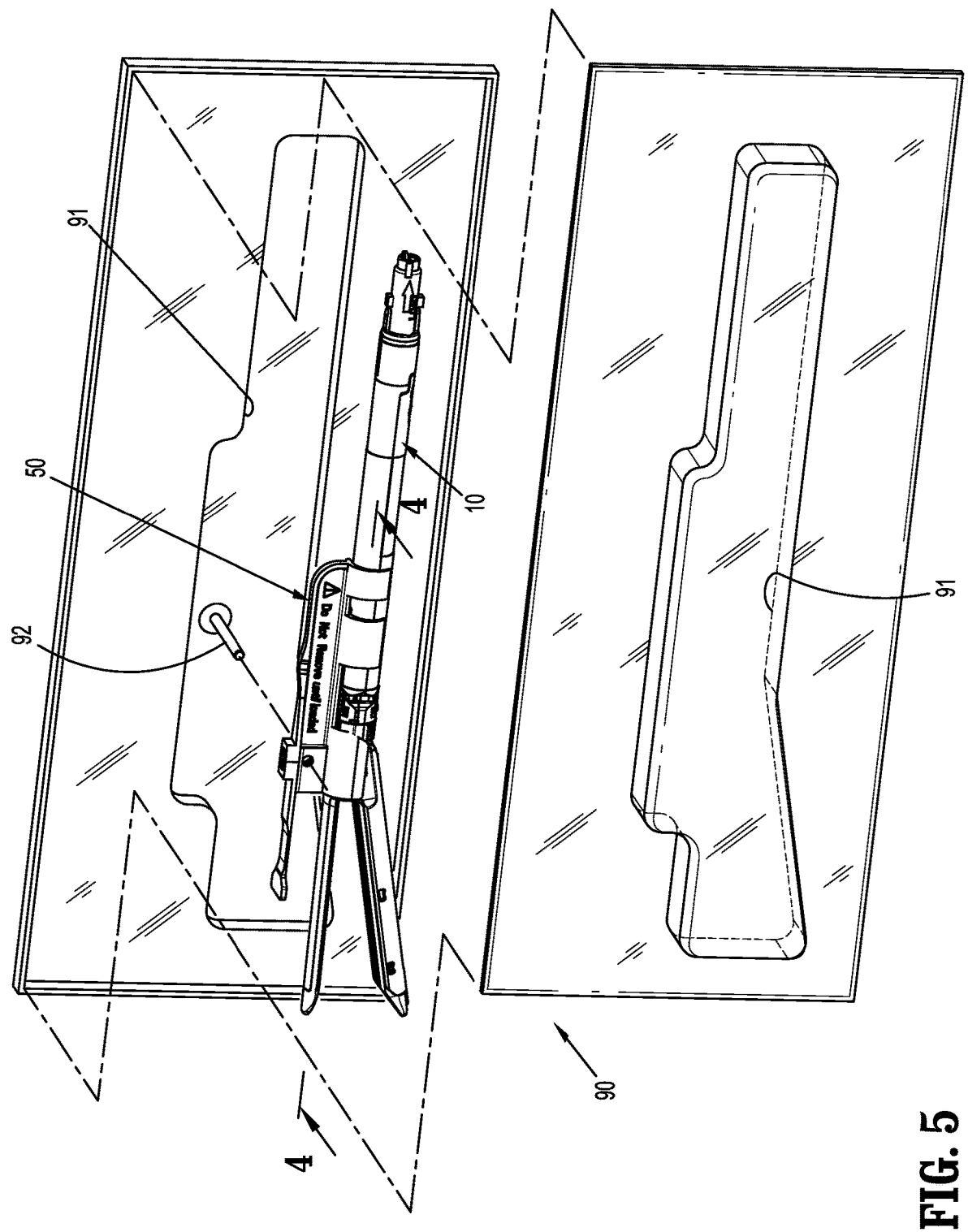
FIG. 5 is a side perspective view of the staple reload and shipping wedge of FIG. 1 in association with a package for storing the staple reload and shipping wedge prior to placement of the staple reload within the package.
Figure 6:
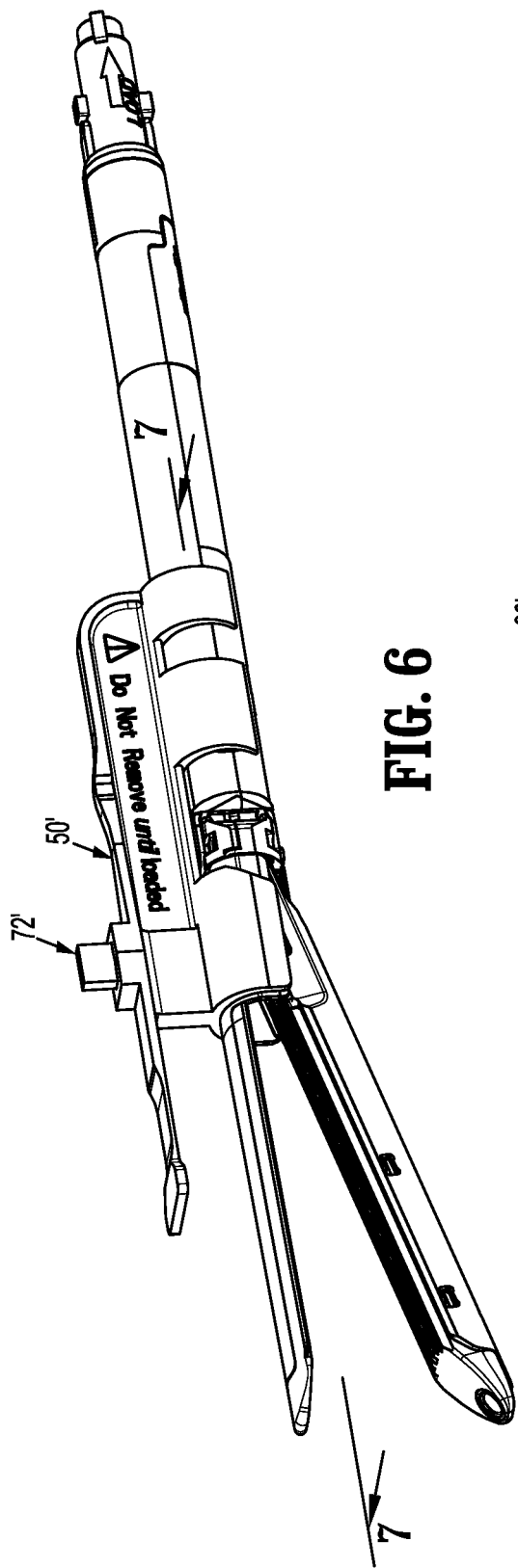
FIG. 6 is a side perspective view of the staple reload shown in FIG. 1 including an actuation sled in association with another exemplary embodiment of a shipping wedge for detecting the presence of the actuation sled within the tool assembly of the staple reload with the tool assembly in an open position.

Referring to FIG. 5, after the reload 10 is manufactured and the shipping wedge 50 is secured to the staple reload 10, the staple reload 10 and the shipping wedge 50 assembly is placed in a sterile package 90 for shipping and storage. In this embodiment, the package 90 defines a cavity 91 that includes a post 92 that is positioned within the package 90. The post 92 is positioned to be received through the bore 70 of the slide 72 and the bore 80 of the slide 72 when the slide 72 is in the first position (FIG. 3) with an actuation sled 54 located within the tool assembly 14. If there is no actuation sled 54 within the tool assembly 14, the slide 72 remains in the second position in which the bore 70 of the slide 72 and the bore 80 of the slide 72 are not aligned with each other. Thus, the staple reload 10 and the shipping wedge 50 assembly cannot receive the post 92 within the cavity 91 of the package 90 and cannot be received within the cavity 91. This provides a clear indication to the manufacturer that the tool assembly 14 does not have an actuation sled 54 and should be discarded.

FIGS. 6-9 illustrate an alternate exemplary embodiment of a shipping wedge in accordance with the disclosure shown generally as 50'. The shipping wedge 50' is substantially identical to the shipping wedge 50 described above but does not include a bore 70 in the housing portion 60' of the shipping wedge 50' or a bore 80 in the slide 72'. In contrast, the slide 72' extends from the housing portion 60' of the shipping wedge 50' when the actuation sled 54 of the staple reload 10 is present and the slide 72' is in the first position and extends through the slot 40a in the bottom wall 40 of the channel 38 of the cartridge assembly 22 when the actuation sled 54 is not present in the tool assembly 14.

Figure 7:
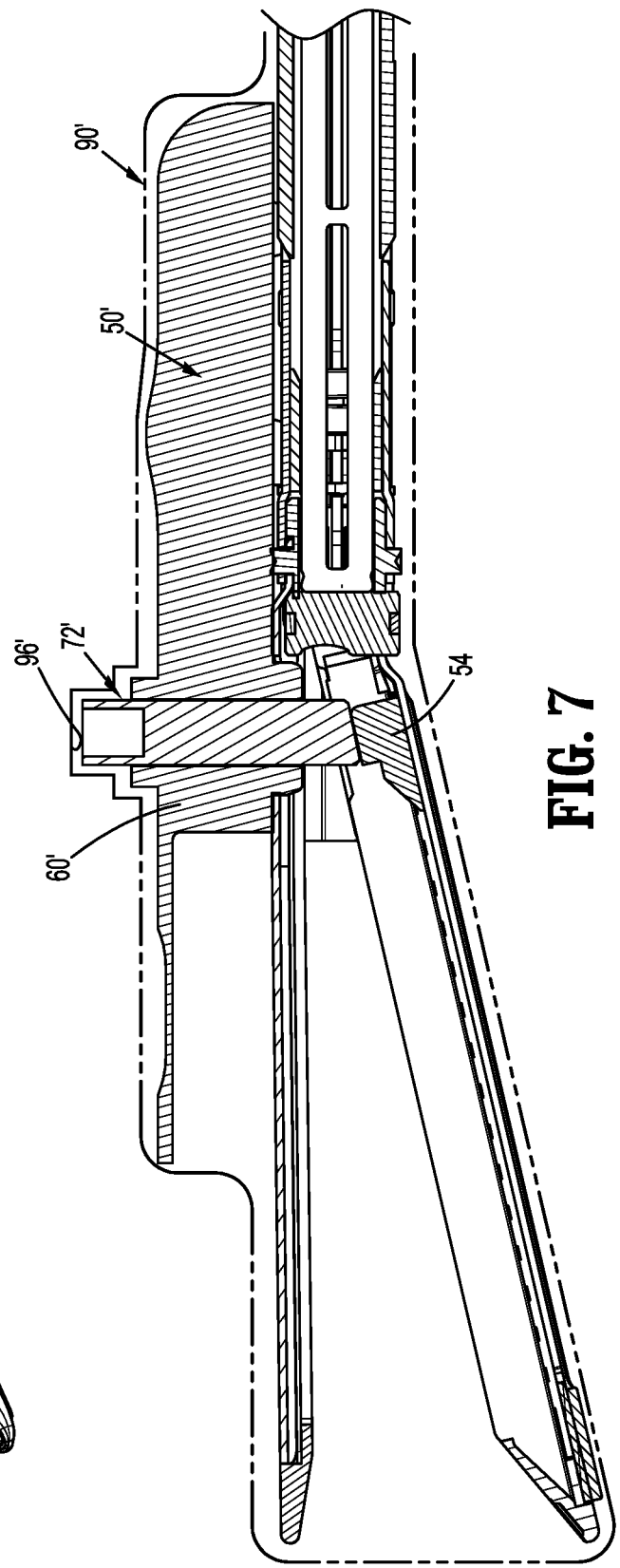
FIG. 7 is a cross-sectional view taken along section line 7-7 of FIG. 6.
Figure 8:
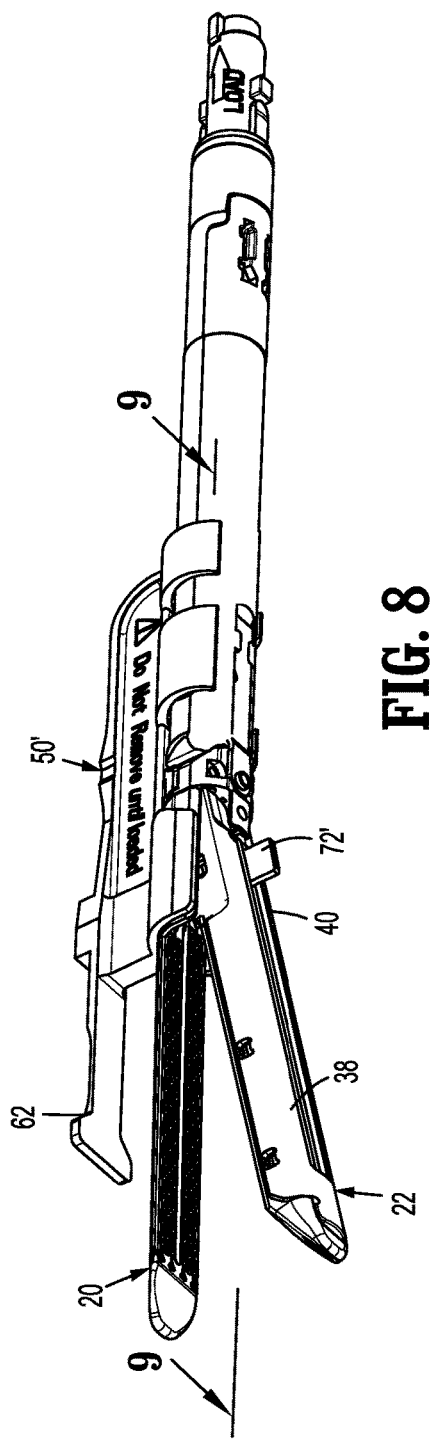
FIG. 8 is a side perspective view of the staple reload and the shipping wedge shown in FIG. 6 with the tool assembly of the staple reload in an open position and the actuation sled missing from the tool assembly.
Figure 9:
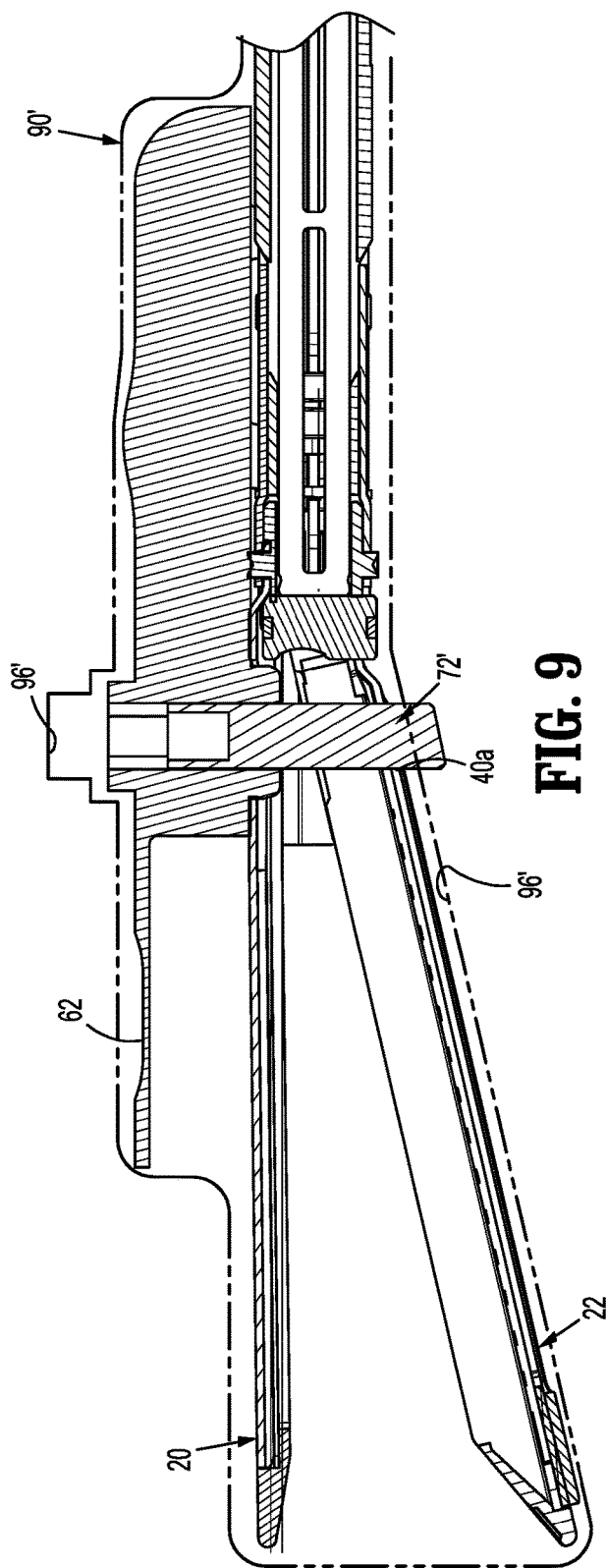
FIG. 9 is a cross-sectional view taken along section line 9-9 of FIG. 8.
Figure 12:
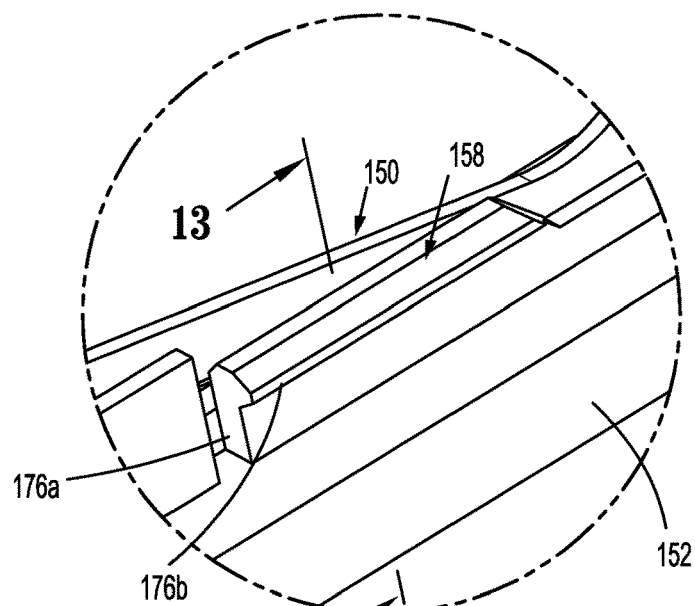
FIG. 12 is an enlarged view of the indicated area of detail shown in FIG. 10.
Figure 13:
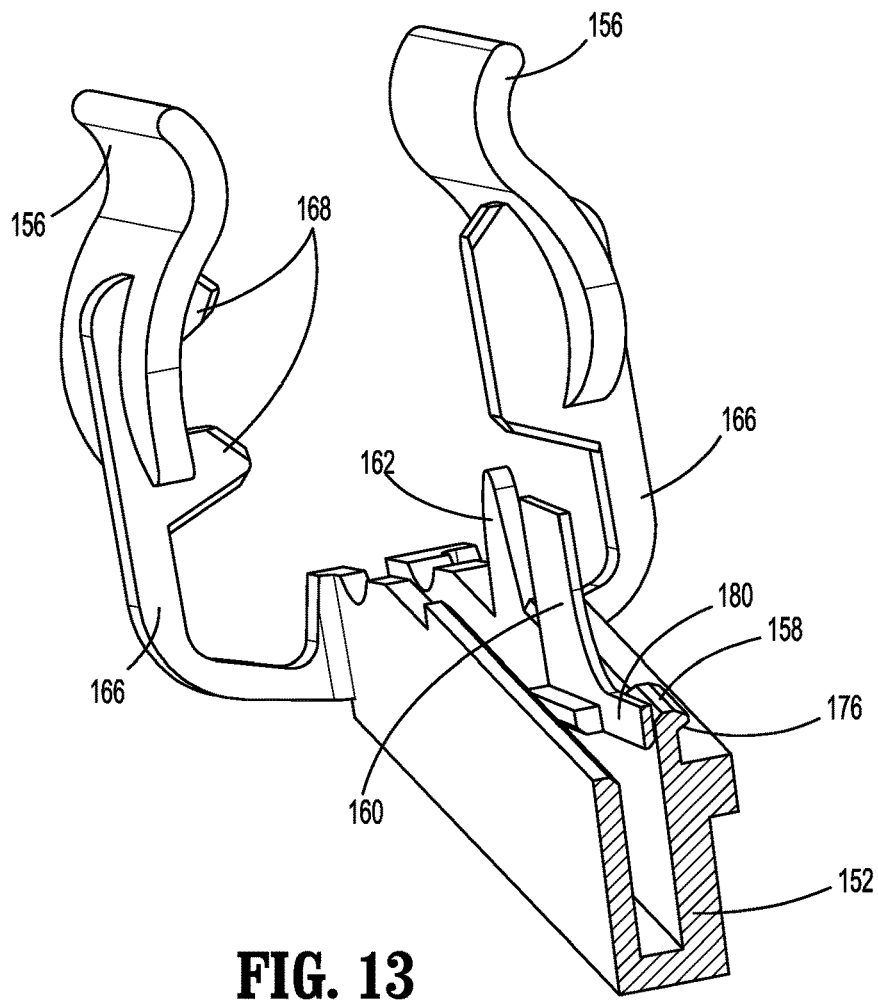
FIG. 13 is a cross-sectional view taken along section line 13-13 of FIG. 12.
Figure 14:
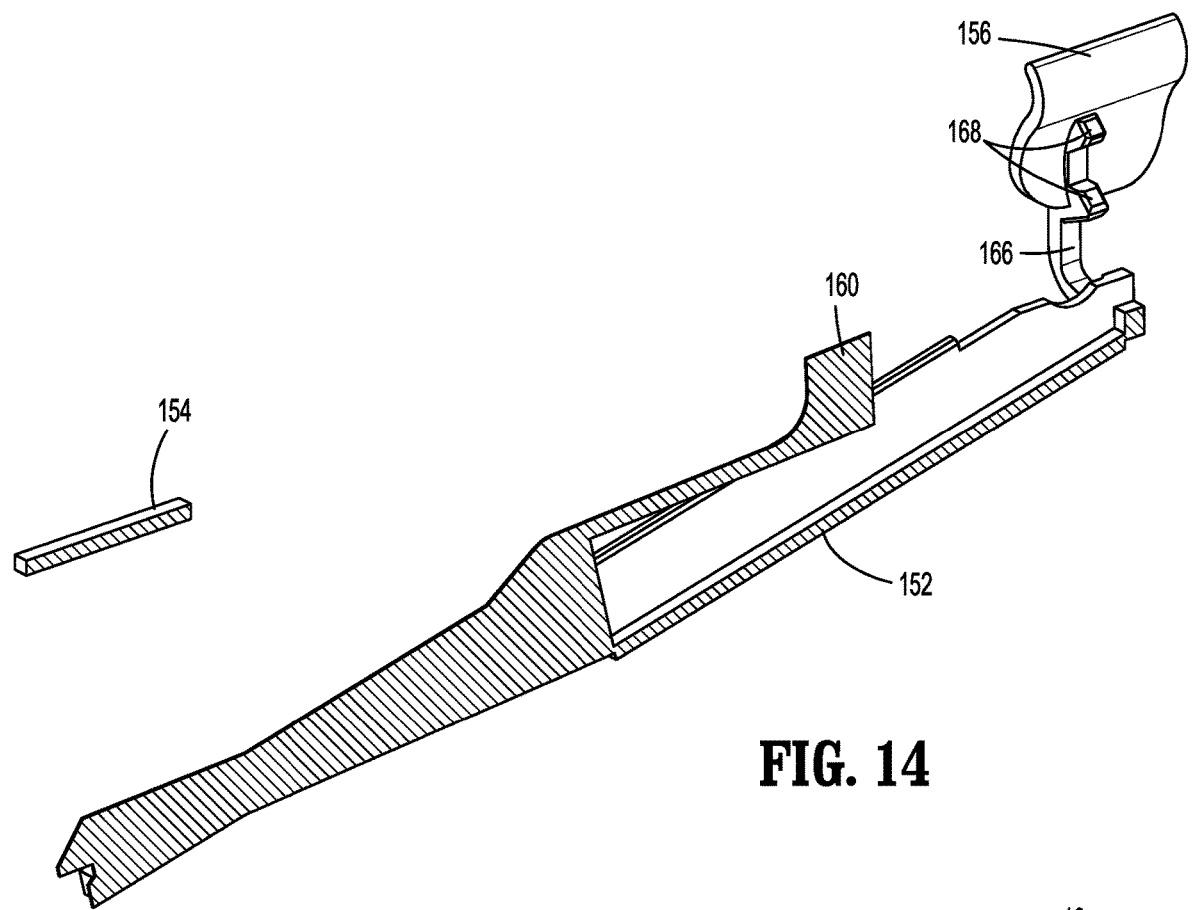
FIG. 14 is a cross-sectional view taken along section line 14-14 of FIG. 10.

When the staple reload 10 and the shipping wedge 50' assembly are placed within the blister package 90' after manufacturing, a cavity 96' defined by the package 90' is configured to only receive the staple reload 10 and shipping wedge 50' when the slide 72' is in the first position (FIG. 7). As shown in FIG. 9, the slide 72' will not fit in the cavity 96' of the package 90' when the slide 72' is in the second position (FIG. 9). This provides a clear indication to the manufacturer that the tool assembly 14 does not have an actuation sled 54 and should be discarded. Although not shown, a biasing member such as biasing member 74 may be provided to urge the slide 72' to the second position (FIG. 9).

Figure 15:
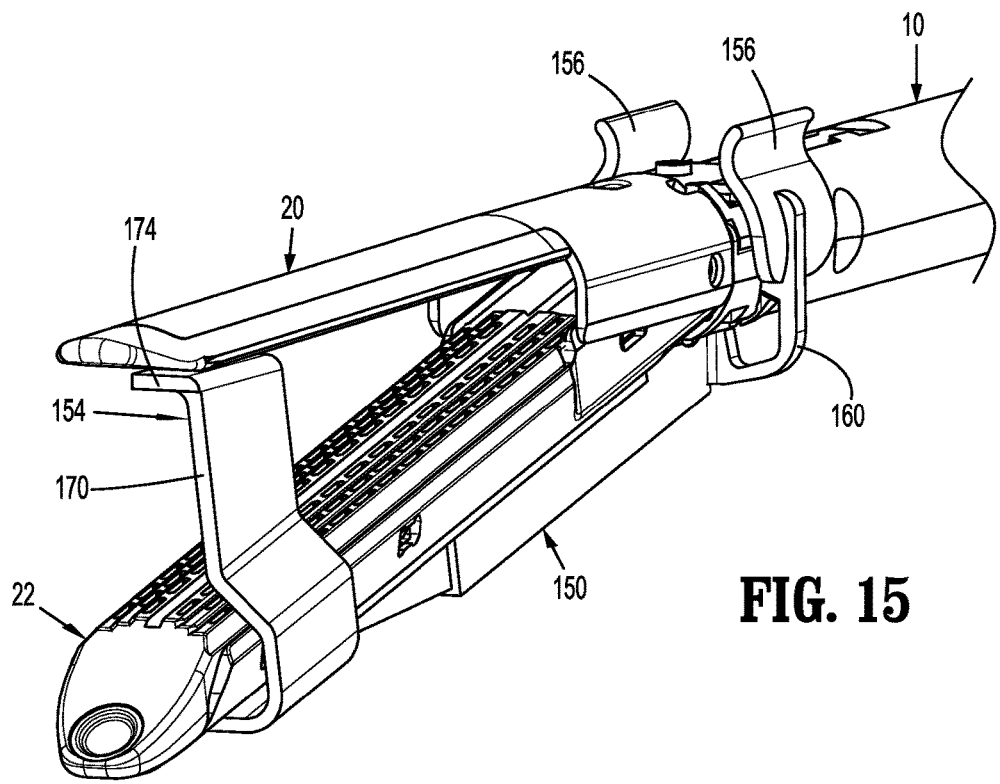
FIG. 15 is a side perspective view of the staple reload shown in FIG. 1 in association with another exemplary embodiment of a shipping wedge for detecting the presence of the actuation sled within the tool assembly of the staple reload with the tool assembly in an open position.
Figure 16:
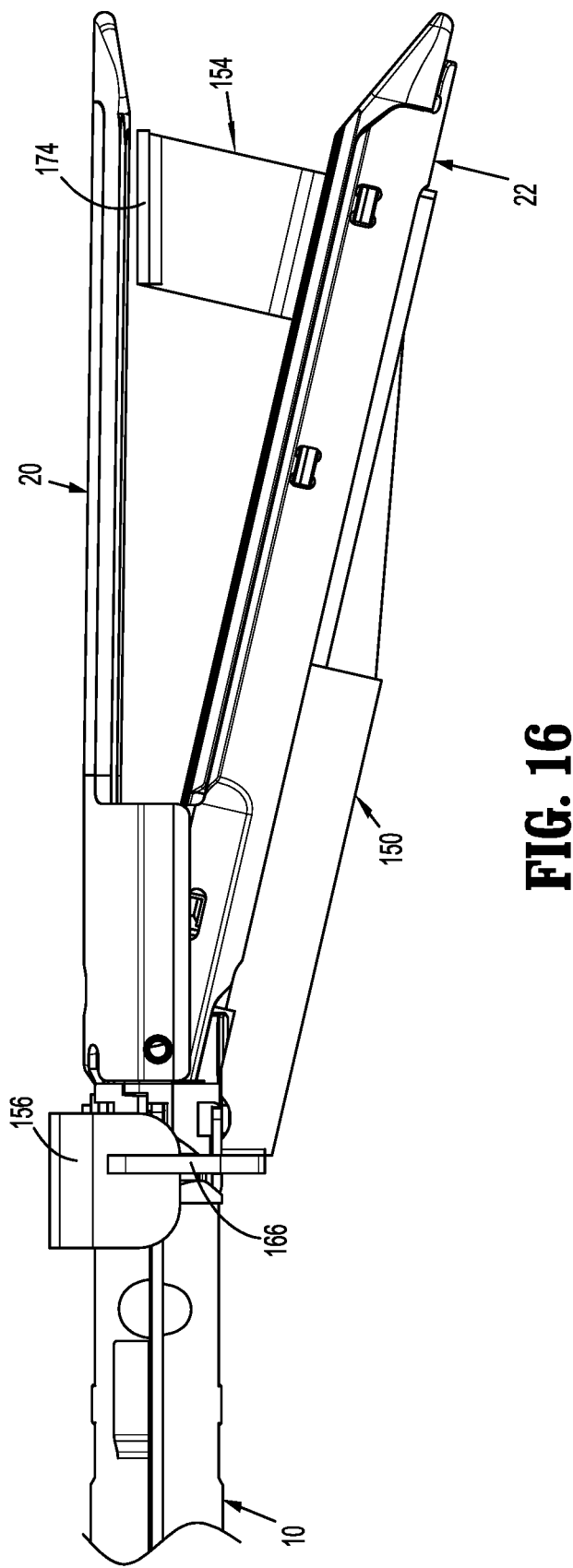
FIG. 16 is a side view of the staple reload and shipping wedge shown in FIG. 10.
Figure 17:
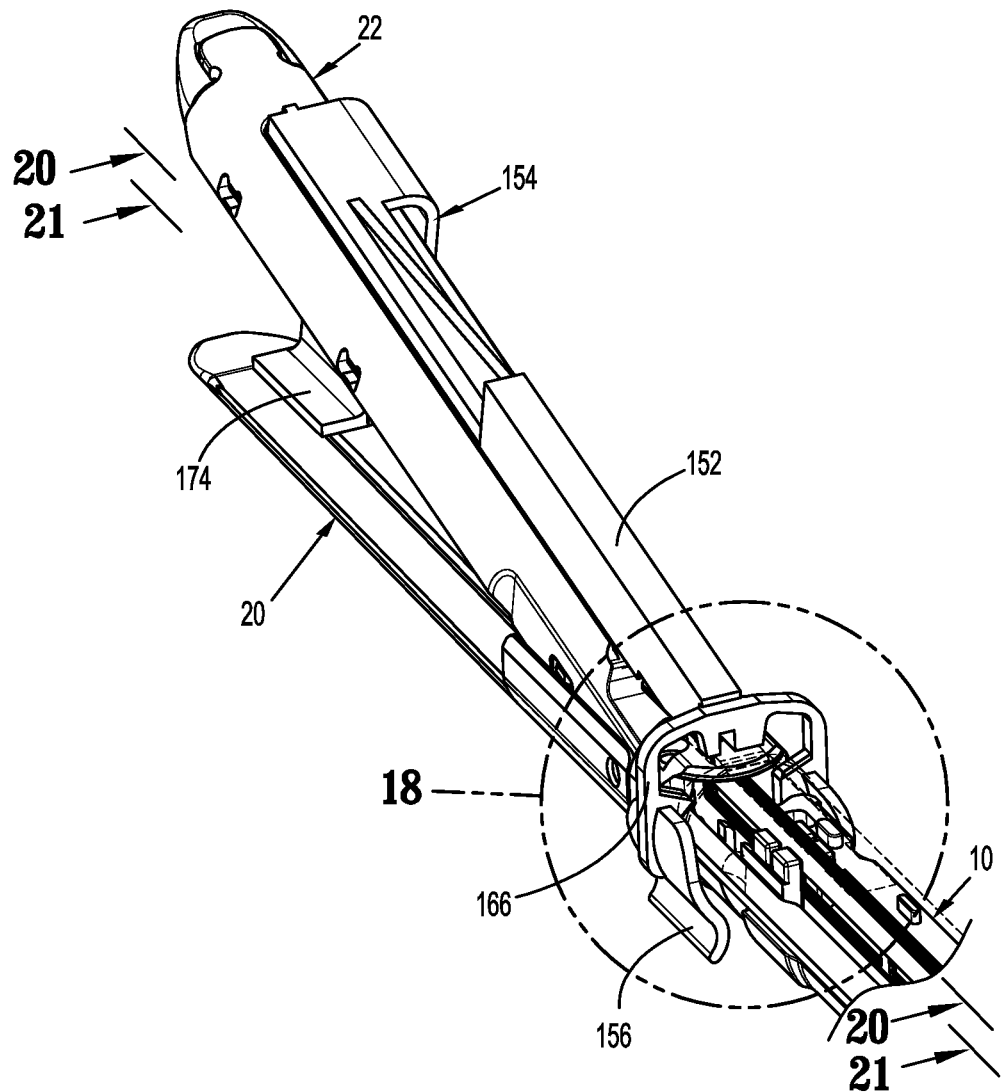
FIG. 17 is a perspective view from the proximal end of the tool assembly of the staple reload shown in FIG. 10 with a tubular housing of a proximal body portion of the staple reload removed and the tool assembly in the open position.
Figure 19:
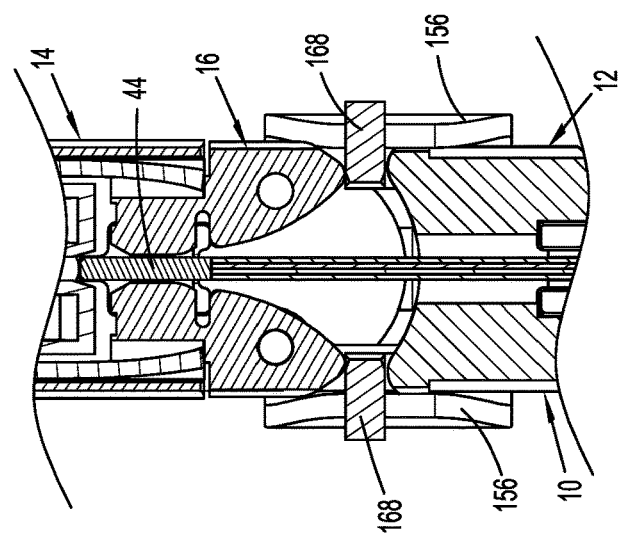
FIG. 19 is a cross-sectional view taken along section line 19-19 of FIG. 18.
Figure 18:
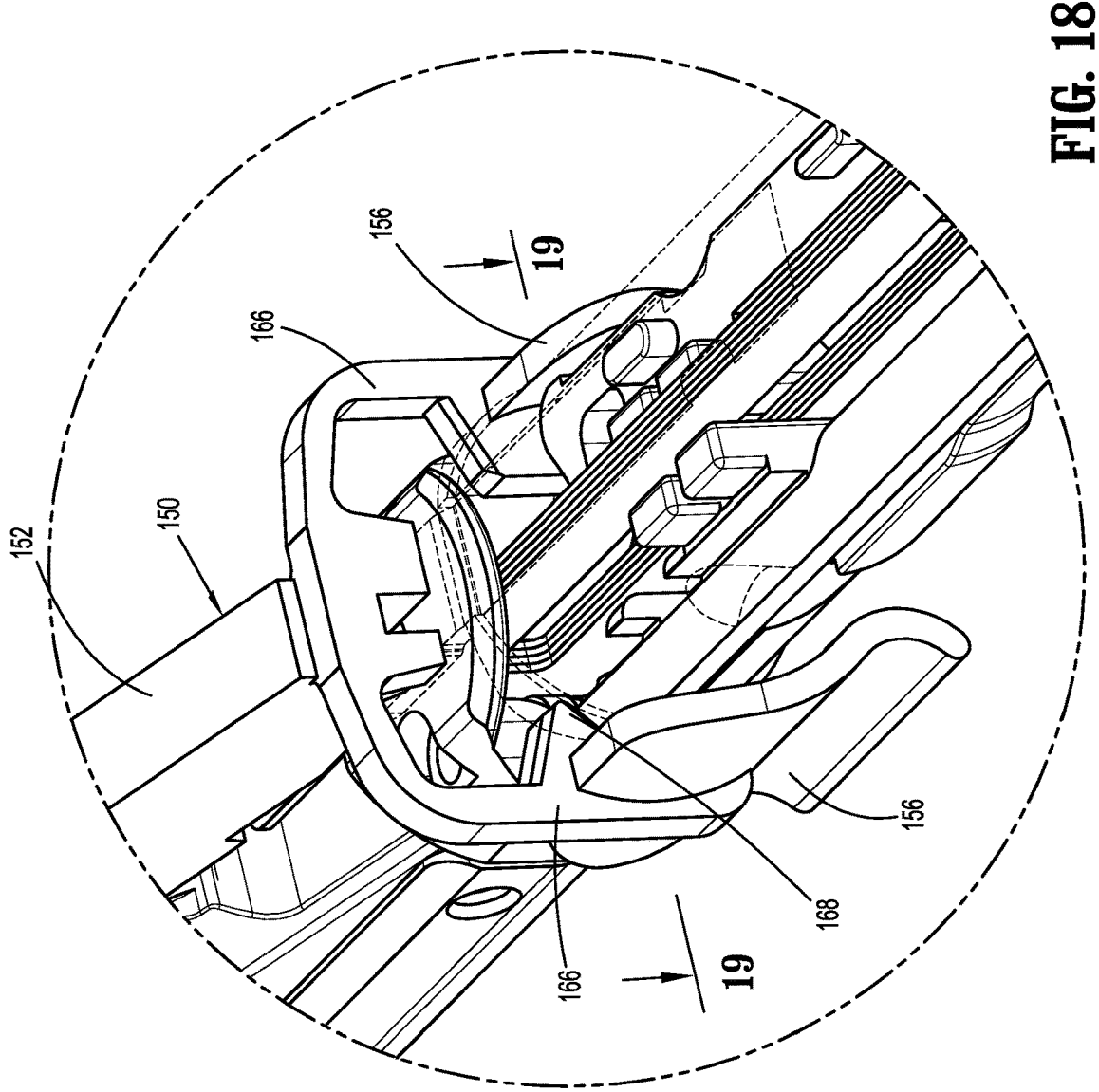
FIG. 18 is an enlarged view of the indicated area of detail shown in FIG. 17.

FIGS. 10-24 illustrate an alternate embodiment of the disclosed shipping wedge shown generally as shipping wedge 150. FIGS. 10-13 illustrate the shipping wedge 150 which includes a central body portion 152 having a proximal portion and a distal portion, and a spacer 154 that extends from the distal portion of the central body portion 152. The shipping wedge 150 also includes a pair clip members 156 that extend from the proximal portion of the central body portion 152, a retaining member 158, a detection member 160, and a stop member 162. The clip members 156 are each supported on a flexible arm 166 that extend from the central body portion 152 and are configured to engage opposite sides of the staple reload 10 (FIG. 15) to secure the proximal portion of the shipping wedge 150 to the staple reload 10 (FIG. 15). Each of the clip members 156 includes inwardly extending fingers 168 (FIG. 19) that are positioned and configured to be received between the mounting assembly 16 and the proximal body portion 12 of the staple reload 10 to secure the distal portion of the shipping wedge 150 to the staple reload 10 and to prevent articulation of the tool assembly 14 in relation to the proximal body portion 12.

The spacer 154 is supported on the distal portion of the central body portion 152 and includes a cantilevered leg 170 and a transverse portion 174. The cantilevered leg 170 extends outwardly from the central body portion 152 and defines a channel 172 with the central body portion 152 that is dimensioned to receive a distal portion of the cartridge assembly 22 (FIG. 15). The transverse portion 174 is positioned to engage the anvil 20 of the tool assembly 14 when the shipping wedge 150 is secured to the staple reload 10 to maintain the anvil 20 and the cartridge assembly 22 in the open position (FIG. 15).

Figure 22:
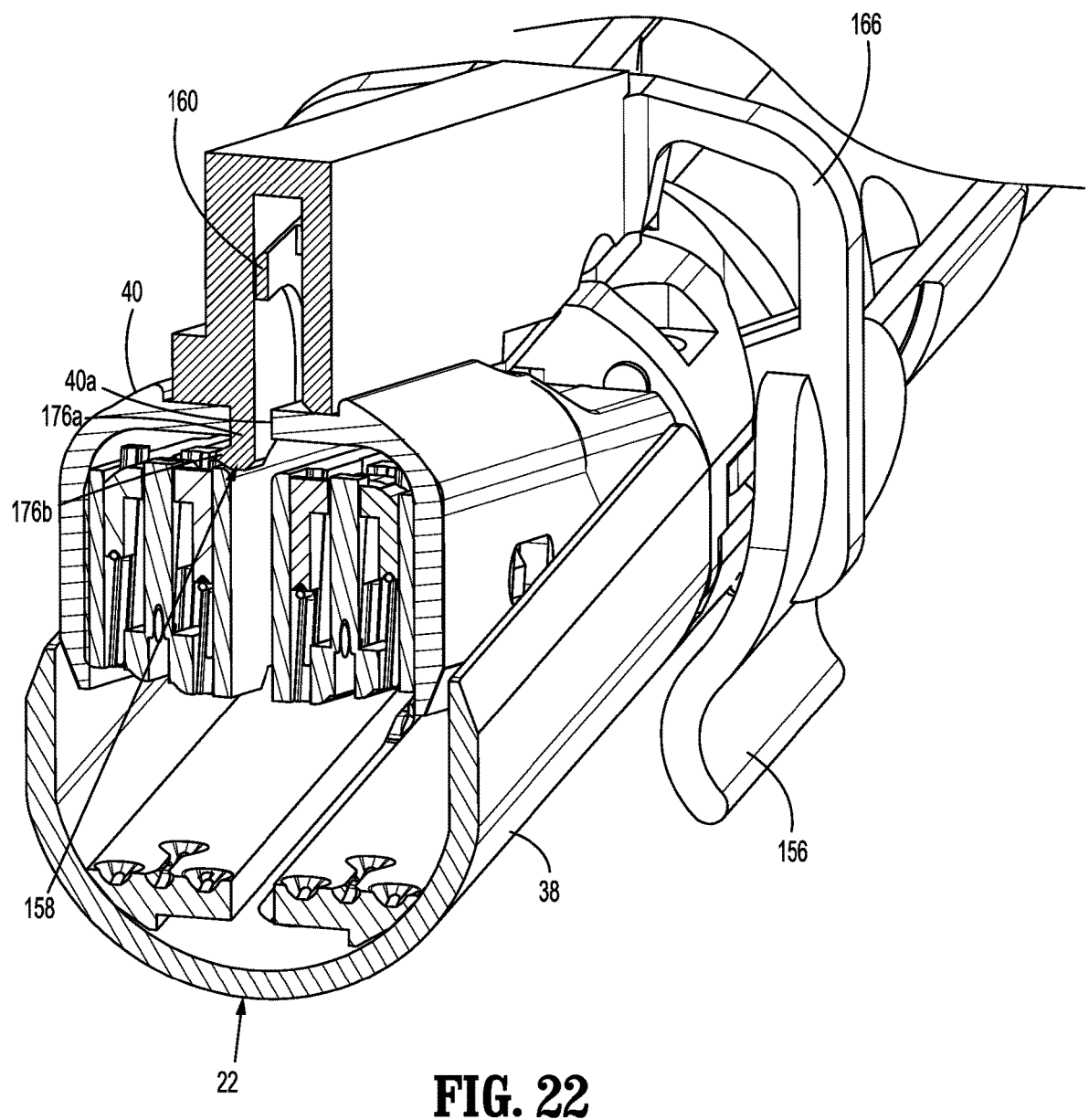
FIG. 22 is a cross-sectional view taken along section line 22-22 of FIG. 21.
Figure 23:
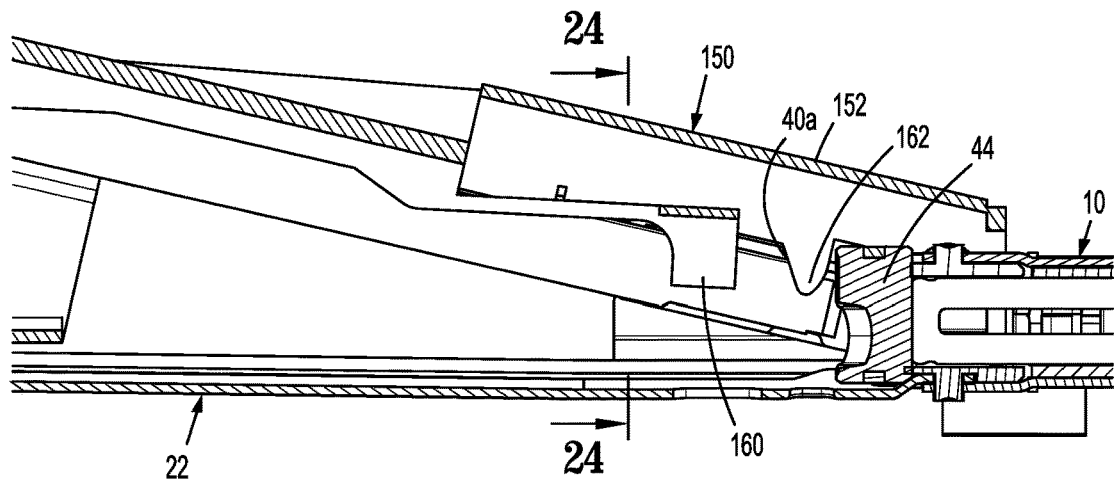
FIG. 23 is a side cross-sectional view taken along section line 21-21 with the actuation sled removed from the staple cartridge.

FIGS. 15-24 illustrate the shipping wedge 150 supported on the staple reload 10. The stop member 162 of the shipping wedge 150 is positioned on the central body portion 152 of the shipping wedge 150 and is configured to be received within the slot 40a (FIG. 9) defined in the bottom wall 40 of the channel 38 of the cartridge assembly 22 to a position distally of the knife bar 44 of the drive assembly 42 (FIG. 23). The stop member 162 prevents inadvertent advancement of the drive assembly 42 during shipping and storage.

Figure 24:
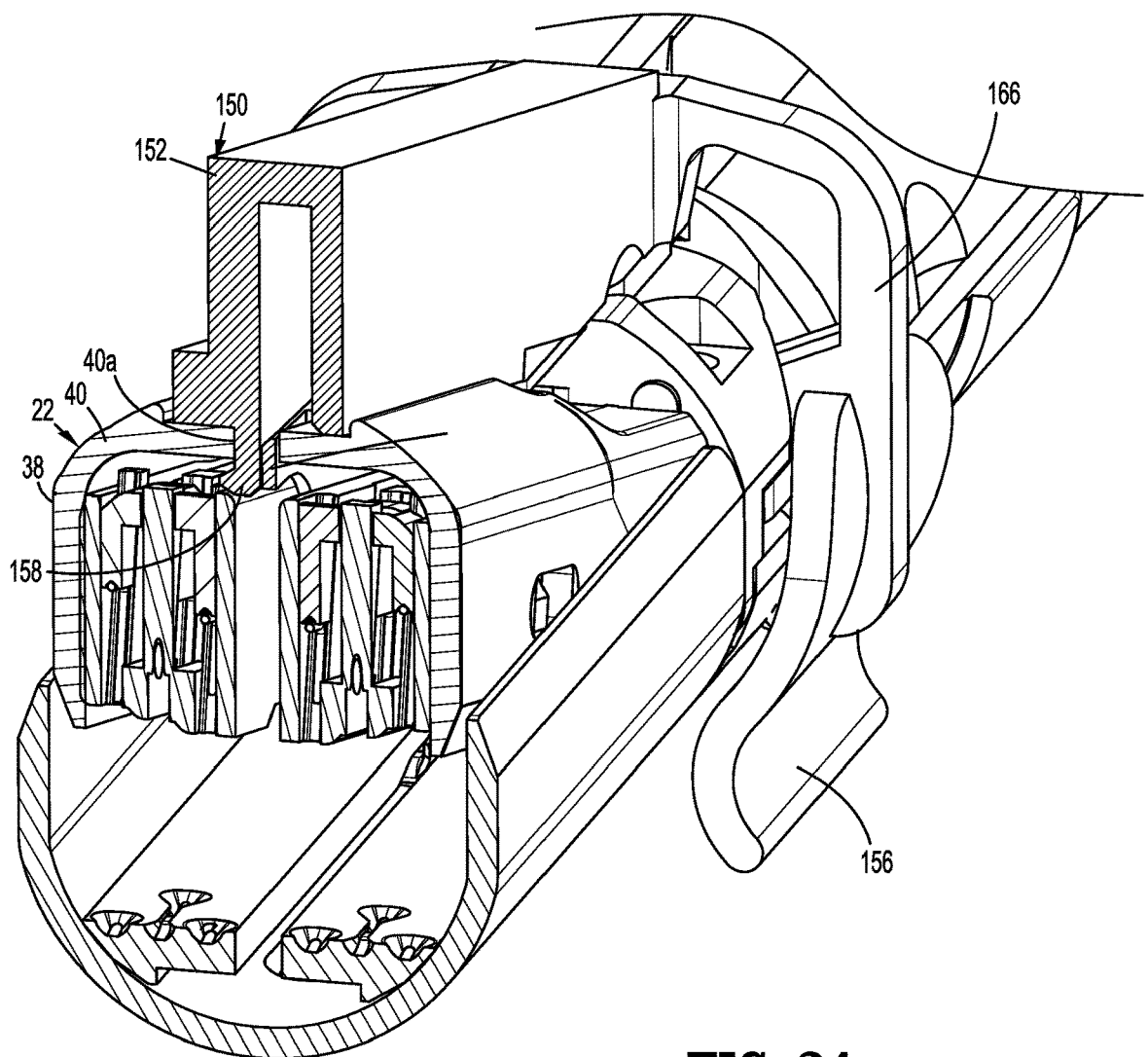
FIG. 24 is a cross-sectional view taken along section line 24-24 of FIG. 23.
Figure 29:
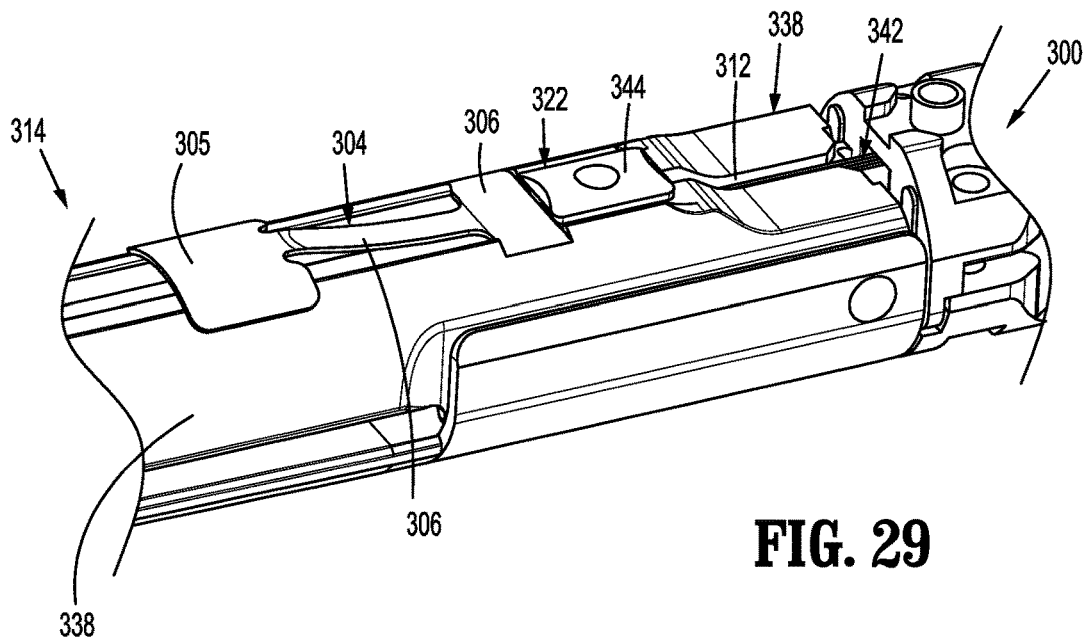
FIG. 29 is a side perspective view of an exemplary embodiment of a tool assembly of a staple reload without an actuation sled including a lockout mechanism for a knife bar of the staple reload with the lockout mechanism in a locked position.

The retaining member 158 of the shipping wedge 150 is also dimensioned to be received through the slot 40a in the bottom wall 40 of the channel 38 of the cartridge assembly 22 (FIG. 24). The retaining member 158 includes a vertical strut 176a (FIG. 12) and a transverse shoulder 176b. The vertical strut 176a extends through the slot 40a in the bottom wall 40 of the channel 38 of the cartridge assembly 22. When the retaining member 158 is received within the slot 40a of the channel 38 of the cartridge assembly 22, the transverse shoulder 176b of the retaining member 158 engages an inner surface of the bottom wall 40 of the channel 38 (FIG. 24) to secure the shipping wedge 150 to the staple reload 10. The slot 40a has a width that is greater than the width of the vertical strut 176a to allow the vertical strut 176a to move within the slot 40a from a locked position in which the shoulder 176b is engaged with the bottom wall 40 of the channel 38 to an unlocked position in which the shoulder 176a of the retaining member 158 is aligned with the slot 40a to facilitate removal of the transverse shoulder 176b from the inner surface of the bottom wall 40. When the vertical strut 176a of the retaining member 158 is moved to the unlocked position, the transverse shoulder 176b is disengaged from the inner surface of the bottom wall 40 of the channel 38 and can be removed from the slot 40a to separate the shipping wedge 150 from the staple reload 10.

The detection member 160 (FIG. 13) is supported on one end of a resilient arm 180. The other end of the resilient arm 180 is connected to the central body portion 152 of the shipping wedge 150. When the shipping wedge 150 is secured to the staple reload 150, the detection member 160 is positioned to engage the actuation sled 54 of the tool assembly 14 of the staple reload 10 (FIG. 21). Upon engagement with the actuation sled 54, the detection member 160 is urged, e.g., pivoted, from a locked position (FIG. 24) to an unlocked position (FIG. 22). In the locked position (FIGS. 23 and 24), where the staple reload 10 does not include an actuation sled 54, the resilient arm 180 is positioned adjacent the vertical strut 176a of the retaining member 158 within the slot 40a of the channel 38 to prevent movement of the vertical strut 176a within the slot 40a of the channel 38 and prevent removal of the shipping wedge 150 from the staple reload 10. In the unlocked position (FIGS. 21 and 22), where the staple reload includes an actuation sled 54, the detection member 160 engages the actuation sled 54 to urge the resilient arm 180 upwardly and remove the resilient arm 180 from the slot 40a of the channel 38 to allow transverse movement of the vertical strut 176a within the slot 40a. When the resilient arm 180 is removed from the slot 40a, the vertical strut 176a of the retaining member 158 of the shipping wedge 150 can be moved within the slot 40a of the channel 38 to facilitate removal of the transverse shoulder 176b from the channel 38 through the slot 40a and thus, allow removal of the shipping wedge 150 from the staple reload 10.

The configuration of the shipping wedge 150 prevents removal of the shipping wedge 150 from the staple reload 10 when the tool assembly 14 does not include an actuation sled 54 to prevent use of the staple reload 10 when an actuation sled 54 is not present within the staple reload 10. This provides a clear indication to a clinician to discard the staple reload 10.

FIGS. 25-28 illustrate another alternate embodiment of the disclosed shipping wedge shown generally as shipping wedge 250. The shipping wedge 250 includes a body 252 that is formed of a resilient material and includes a longitudinal grip portion 254, an extension 256, a detection member 258, a guide member 259, and clip members 260 that extend from the grip portion 254. The extension 256 extends distally from the grip portion 254. The clip members 260 are configured be snap-fit over the staple reload 10 to secure the shipping wedge 250 to the staple reload 10. In embodiments, the clip members 260 are semi-circular in shape and can flex outwardly to receive the staple reload 10. The guide member 259 is received within a guide hole 20a (FIG. 26) formed in the anvil 20 to properly locate the shipping wedge 250 on the stapling reload 10.

The detection member 258 extends from the body 252 in the direction of the clip members 260 and is positioned to extend through the through bore 26 of the anvil 20 into the tool assembly 14. The detection member 258 is supported on a resilient arm 262 that extends from the body 252 of the shipping wedge 250 and includes a curved body 264 having an engagement surface 264a. The curved body 264 includes a cam surface 266 including a locking member or surface. In embodiments, the locking member or surface includes a stepped shoulder 268. The cam surface 266 is positioned to engage an inner wall of the anvil 20 defining the distal end of the through bore 26 when the detection member 258 is inserted through the through bore 26 in the anvil 20.

When the shipping wedge 250 is secured to the staple reload 10, and the detection member 258 is inserted through the through bore 26 of the anvil 20, the engagement surface 264a of the detection member 258 is positioned to engage the actuation sled 54 within the tool assembly 14 to prevent further insertion of the detection member 258 into the tool assembly 258 (FIG. 27). When the engagement surface 264a engages the actuation sled 54, the detection member 258 is biased upwardly in the direction indicated by arrow "B" in FIG. 27 to prevent the locking member, e.g., the stepped shoulder 268, of the detection member 258 from passing through the through bore 26 of the anvil 20 into the tool assembly 14.

Referring to FIG. 28, when an actuation sled 54 is not present in the tool assembly 14 of the staple reload 10, as the shipping wedge 250 is secured to the staple reload 10, the detection member 258 extends through the through bore 26 of the anvil 20 and enters the tool assembly 14 without obstruction by the actuation sled 54. As the detection member 258 passes through the through bore 26 of the anvil 20, the detection member 258 is flexed inwardly as the cam surface 266 of the detection member 258 engages the anvil 20. When the stepped shoulder 268 of the detection member 258 passes through the through bore 26 of the anvil 20, the detection member 258 flexes outwardly in the direction indicated by arrow "C" to move the stepped shoulder 268 of the detection member 258 into engagement with the inner wall defining the through bore 26 of the anvil 20 to prevent removal of the shipping wedge 250 from the staple reload 10.

The configuration of the shipping wedge 250 prevents removal of the shipping wedge 250 from the staple reload 10 when the tool assembly 14 does not include an actuation sled 54 to prevent use of the staple reload 10. This provides a clear indication to a clinician to discard the staple reload 10.

Figure 30:
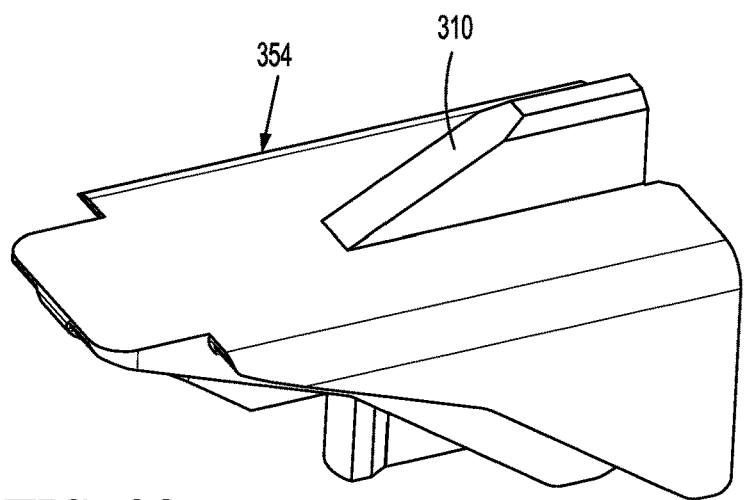
FIG. 30 is a perspective view from the bottom of the an actuation sled of the tool assembly shown in FIG. 29.
Figure 31:
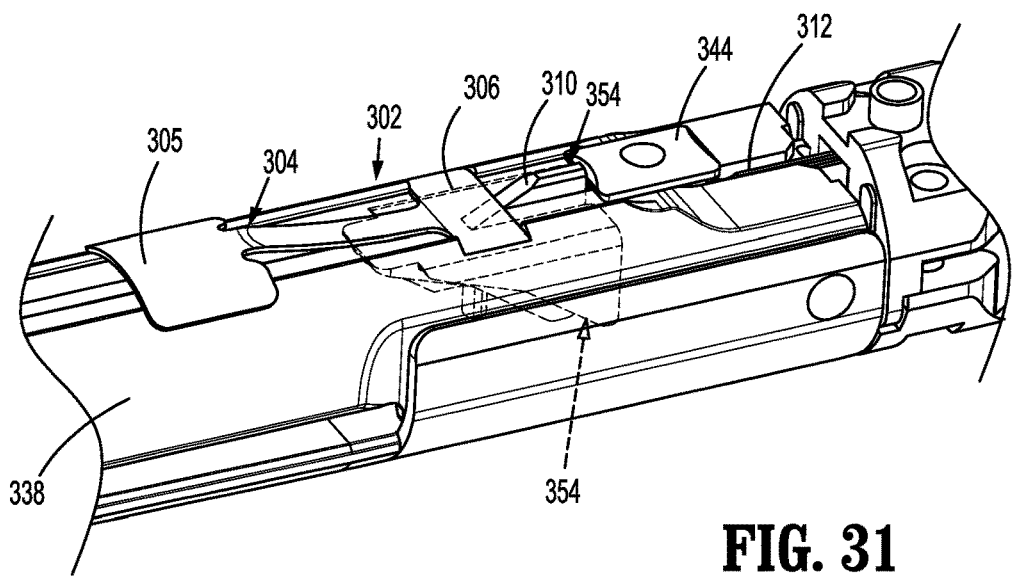
FIG. 31 is a side perspective view of the tool assembly of the staple reload shown in FIG. 29 including an actuation sled with the knife bar and actuation sled in retracted positions.

FIGS. 29-33 includes another exemplary embodiment of a staple reload shown generally as staple reload 300 that includes a mechanism 302 to prevent use of the staple reload 300 when the staple reload 300 is missing an actuation sled 354 (FIG. 31). The staple reload 300 is substantially the same as the staple reload 10 except for the addition of the mechanism 302. The mechanism 302 includes a resilient locking member 304 that includes a base 305 that is secured to the channel 338 of the cartridge assembly 322. The locking member 304 also includes a resilient finger 306 that extends proximally from the base 305 and is positioned distally of a knife bar 344 of a drive assembly 342 of the tool assembly 314 when the knife bar 344 is in a retracted position. In a first unbiased locked position (FIG. 29), the resilient finger 306 is positioned to obstruct distal movement of the knife bar 344 of the drive assembly 342 through the cartridge assembly 322.

Figure 32:
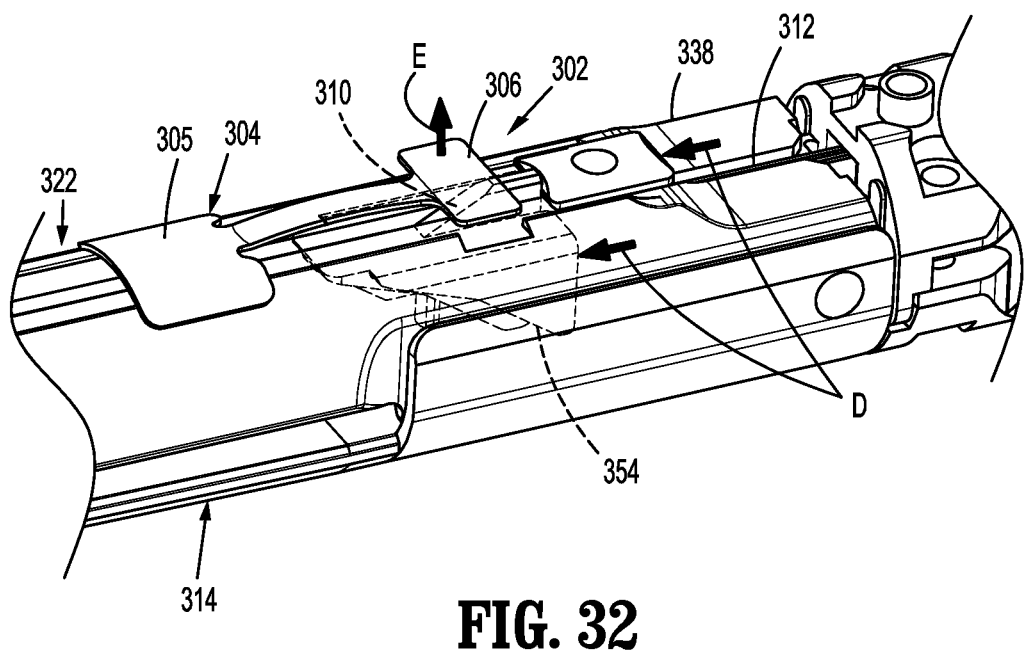
FIG. 32 is a side perspective view of the tool assembly of the staple reload shown in FIG. 31 as the knife bar and actuation sled are moved from their retracted positions towards their advanced positions as the lockout mechanism is moved to its unlocked position.
Figure 33:
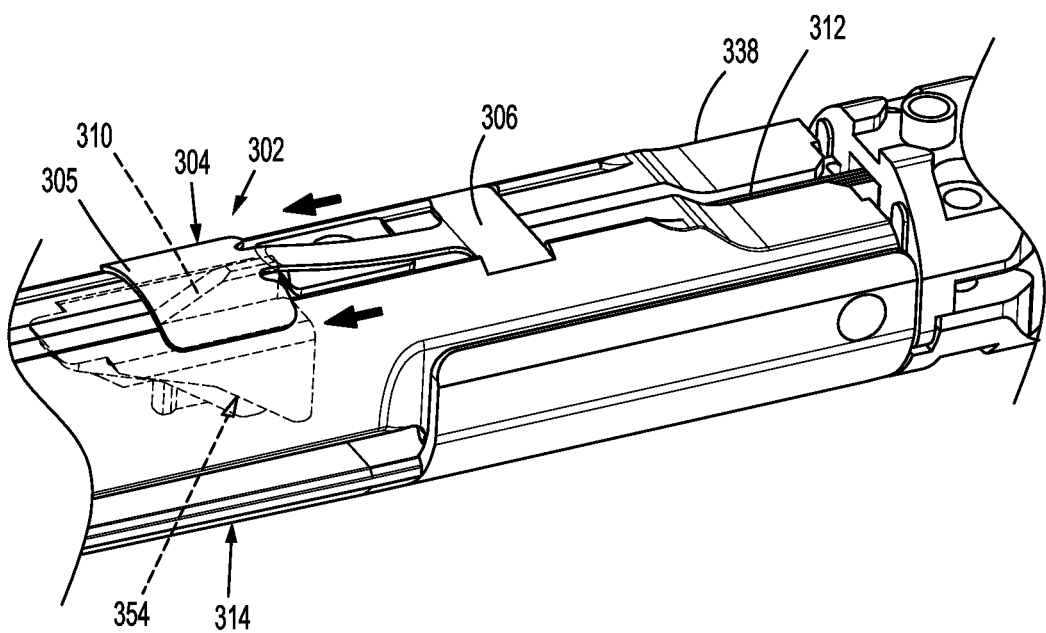
FIG. 33 is a side perspective view of the tool assembly of the staple reload shown in FIG. 32 as the knife bar and actuation sled are moved from their retracted positions further towards their advanced positions and the lockout mechanism is returned to its locked position.

Referring to FIGS. 30-32, the actuation sled 354 (FIG. 30) includes a ramp surface 310 that is positioned between the resilient finger 306 and the knife bar 344 and faces the resilient finger 306. When the actuation sled 354 is positioned within the tool assembly 314, the ramp surface 310 extends through a knife slot 312 in the channel 338 of the cartridge assembly 322. When the knife bar 344 is advanced through the cartridge assembly 322 of the tool assembly 314 in the direction indicated by arrows "D" in FIG. 32, the ramp surface 310 of the actuation sled 354 engages the resilient finger 306 of the mechanism 302 to lift the resilient finger 306 in the direction indicated by arrow "E" in FIG. 32 to an unlocked position out of the path of the knife bar 344. If the actuation sled 354 is missing from the tool assembly 314, the resilient finger 306 remains in the locked position to obstruct advancement of the knife bar 344 distally beyond the resilient finger 306 and, thus, prevents firing of the staple reload 300.

When the knife bar 344 is retracted, the knife bar 344 will engage the resilient finger 306 of the resilient locking member 304 and pass under the locking member 304 as it moves through the tool assembly towards its retracted position. In its retracted position, the knife bar 344 is positioned proximally of the resilient finger 306 of the locking member 304 and is ready for subsequent uses. In devices in which the staple cartridge is reusable such as devices that use multi-use loading units, the locking member 304 will function to lockout the tool assembly wherein newly loaded staple cartridges do not include an actuation sled.

Figure 36:
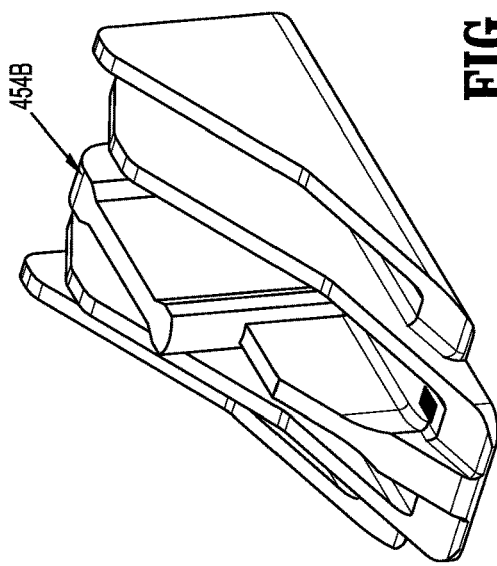
FIG. 36 is another exemplary embodiment of an actuation sled of a tool assembly of a staple reload in accordance with the disclosure.
Figure 34:
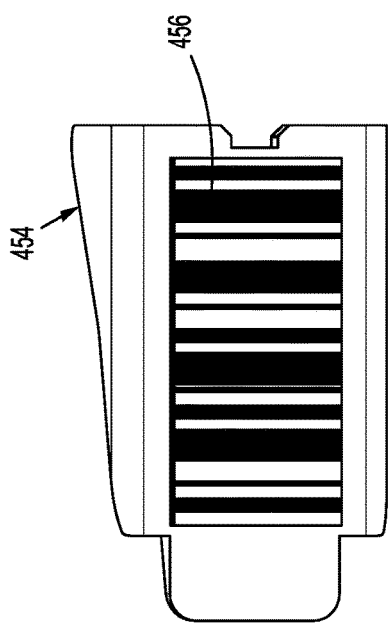
FIG. 34 is a bottom view of another exemplary embodiment of an actuation sled of a tool assembly of a staple reload in accordance with the disclosure.
Figure 35:
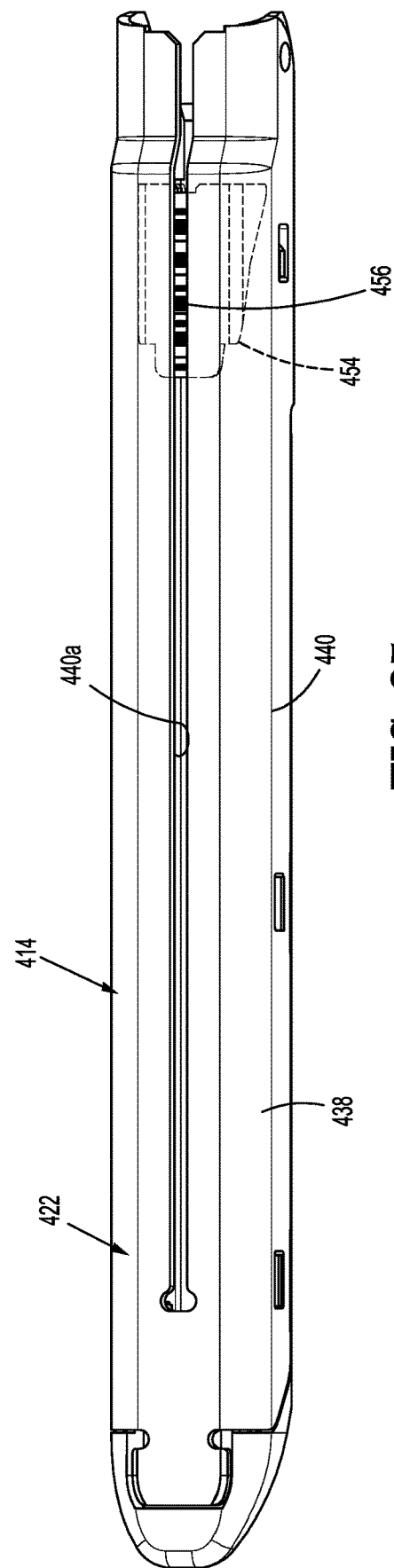
FIG. 35 is a bottom perspective view of a tool assembly including the actuation sled shown in FIG. 34.

FIGS. 34-36 illustrate another exemplary embodiment of a staple reload that allows a manufacturer to identify the absence of an actuation sled 454 within a tool assembly 414 of the staple reload. The actuation sled 454 of the tool assembly 414 includes a barcode 456 that can be read through a slot 440a formed in the channel 440 of the cartridge assembly 422. In embodiments, the slot 440a may be the knife slot or, alternately, the slot could be a slot formed specifically to provide access the barcode. Although the slot 440a is illustrated as being formed in the channel 438 of the cartridge assembly 422, the slot 440a can be formed in any portion of the tool assembly to provide access to a barcode supported on the actuation sled 454.

In an alternate embodiment, the bar code can be replaced with a radio frequency identification tag ("RFID") that is affixed to the actuation sled 454B (FIG. 36). In both embodiments, the tool assembly 414 is scanned to determine the presence or absence of an actuation sled 454 within the tool assembly 414. It is envisioned that the actuation sled 454 can be provided with any identifier that can be read from a location externally of the tool assembly to facilitate confirmation of the presence of the actuation sled 454 within the tool assembly including an RFID, a bar code, a chip, a transceiver, a transponder or the like, whether or not identification is accomplished through radio waves, optics, or other known technology.

FIGS. 37-42 illustrate another exemplary embodiment of a staple reload shown generally as staple reload 700 that includes another exemplary embodiment of the disclosed shipping wedge shown generally as shipping wedge 600.

Figure 41:
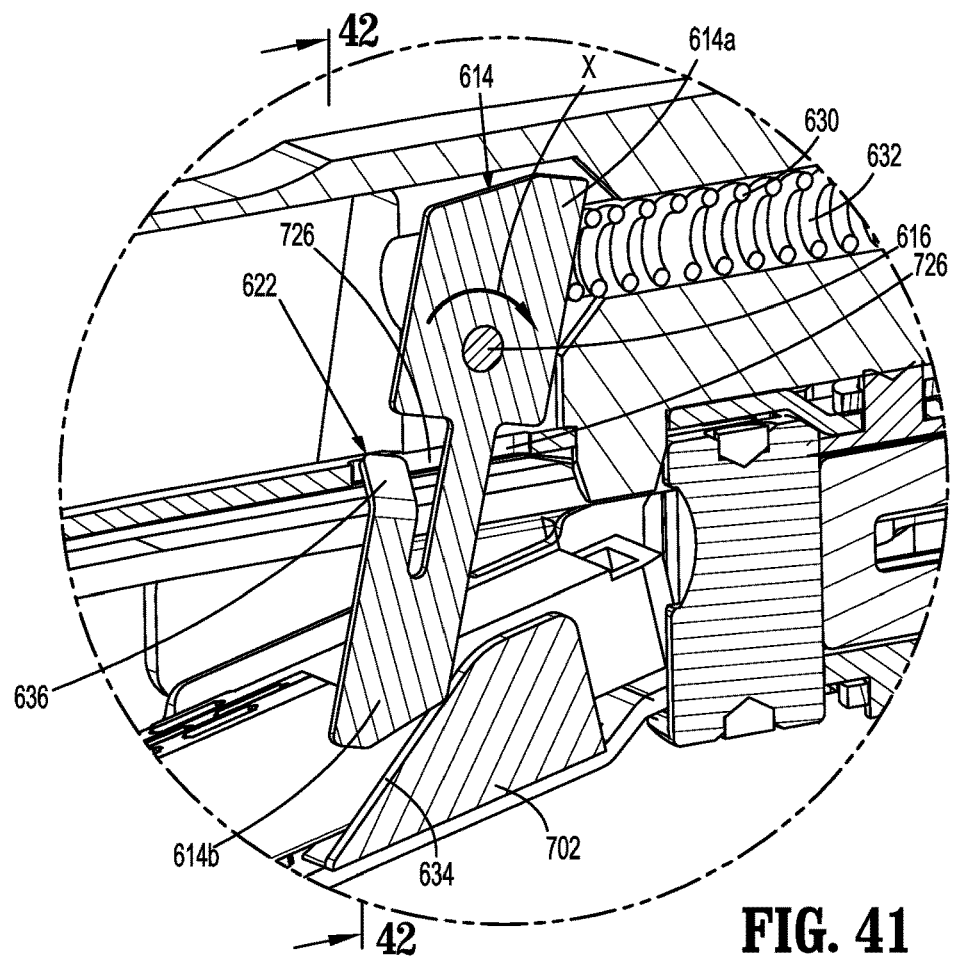
FIG. 41 is an enlarged view of the indicated area of detail shown in FIG. 38 illustrating the reload with an actuation sled.

The shipping wedge 600 prevents use of the staple reload 700 when the staple reload 700 is missing an actuation sled 702 (FIG. 41). The shipping wedge 600 includes a body 602 that is formed of a resilient material and includes a longitudinal grip portion 604, an extension 606, a detection member 608, and clip members 610 that extend from the grip portion 604. The extension 606 extends distally from the grip portion 604 and includes a tab 606a that can be grasped by a clinician to facilitate removal of the shipping wedge 600 from the staple reload 700. The clip members 610 have a semi-circular configuration and can be snap-fit over the staple reload 700 to secure the shipping wedge 600 to the staple reload 700. In embodiments, the clip members 610 are semi-circular in shape and can flex outwardly to receive the staple reload 700.

Figure 37:
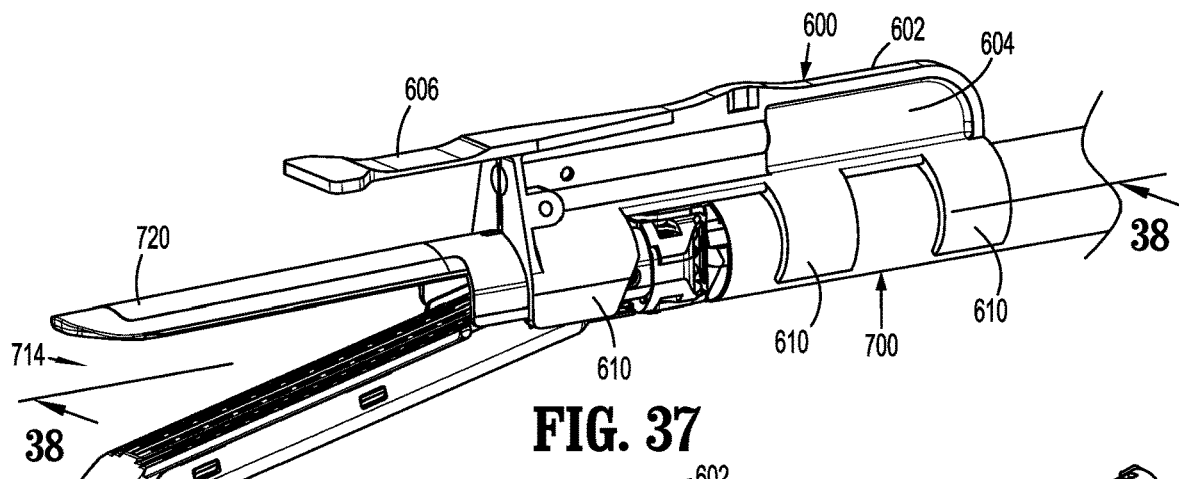
FIG. 37 is a side perspective view of another exemplary embodiment of a staple reload and a shipping wedge for detecting the presence of an actuation sled within a tool assembly of the staple reload with the tool assembly in an open position.
Figure 37A:
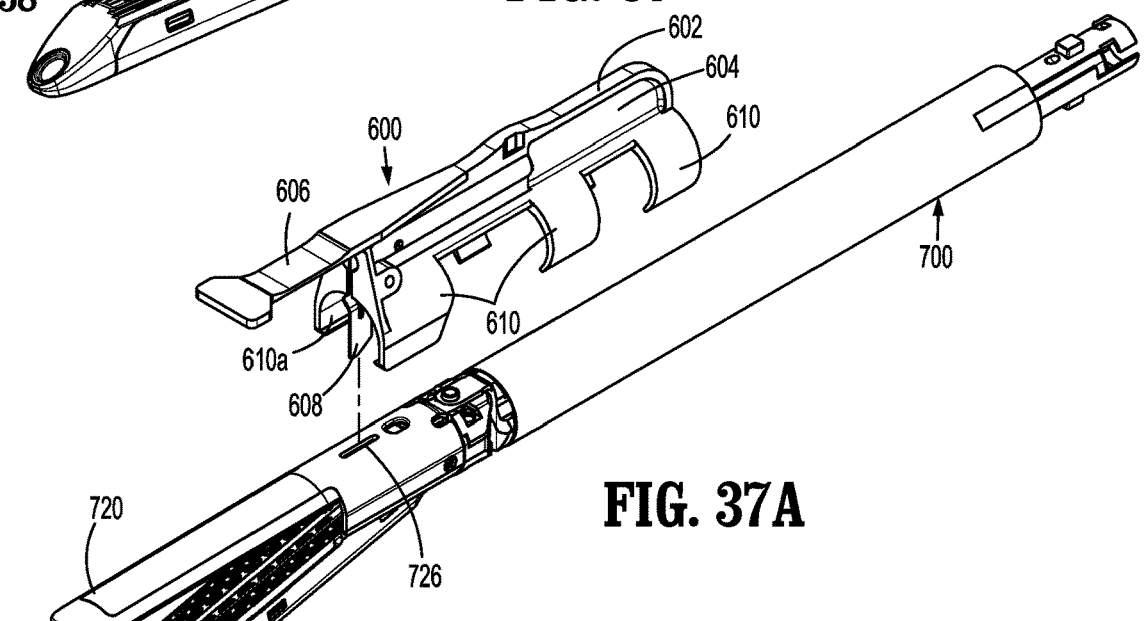
FIG. 37A is a side perspective view of the staple reload and the shipping wedge shown in FIG. 37 with the tool assembly of the staple reload in the open position and the shipping wedge separated from the tool assembly.

The detection member 608 extends from the body 602 of the shipping wedge 600 in the direction of the clip members 610 and is positioned to extend through a through bore 726 (FIG. 37A) defined in an anvil 720 of the tool assembly 714. In embodiments, the detection member 608 is positioned within a cylindrical recess 610a (FIG. 37A) defined by one of the clip members 610. The detection member 608 includes a body 614 (FIG. 41) having an upper portion 614a that is pivotally coupled to the body 602 of the shipping wedge 600 by a pivot member 616 and a lower portion 614b that includes a locking member 622. The pivot member 616 is centrally positioned on the body 614 of the detection member 608 between the upper and lower body portions 614a and 614b, respectively. The body 602 of the shipping wedge 600 defines a blind bore 630 that is aligned with the upper portion 614a of the detection member 608. The blind bore 630 receives a biasing member 632 that engages the upper portion 614a of the detection member 608 to urge the detection member 608 to rotate about the pivot member 616 in the direction indicated by arrow "Z" in FIG. 39. The lower body portion 614b has an engagement surface 634 (FIG. 39) that is angled towards the upper body portion 614a in the proximal direction.

The locking member 622 includes a resilient finger 636 that extends towards the upper body portion 614a and transversely outwardly from the lower body portion 614b of the locking member 622. The resilient finger 636 is positioned to prevent the detection member 608 from being removed from the anvil 720 of the tool assembly 714 when the resilient finger 636 passes through the slot 726 to prevent removal of the shipping wedge 600 from the staple reload 700 to effectively disable the staple reload 700.

Figure 38:
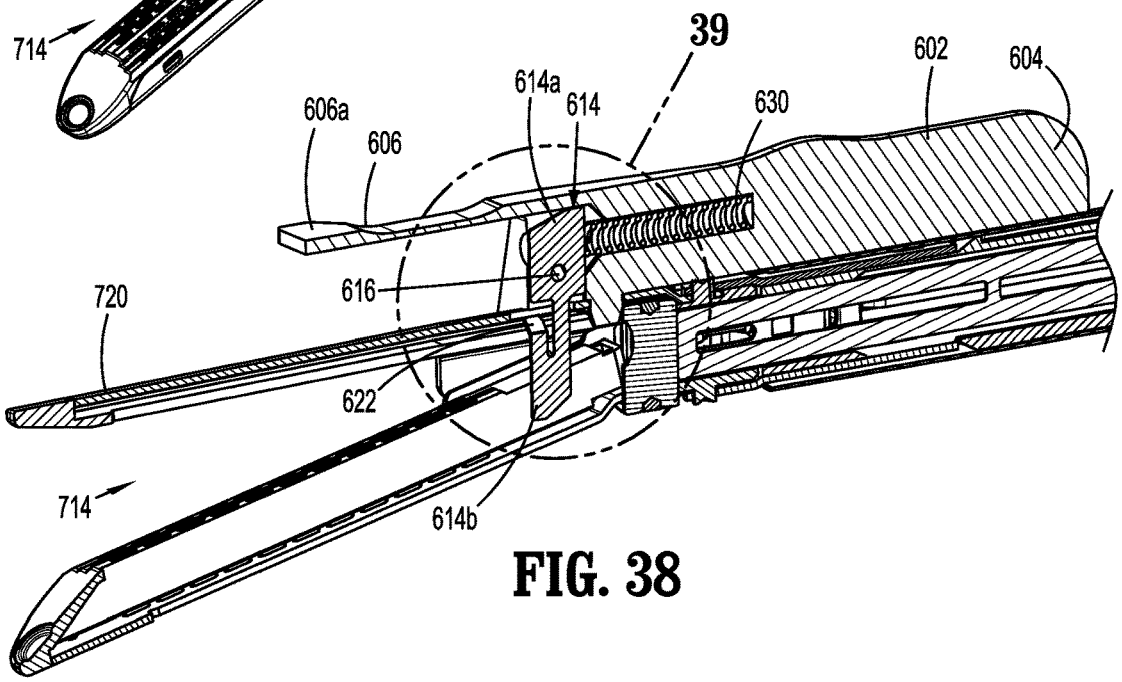
FIG. 38 is a cross-sectional view taken along section line 38-38 of FIG. 37.
Figure 39:
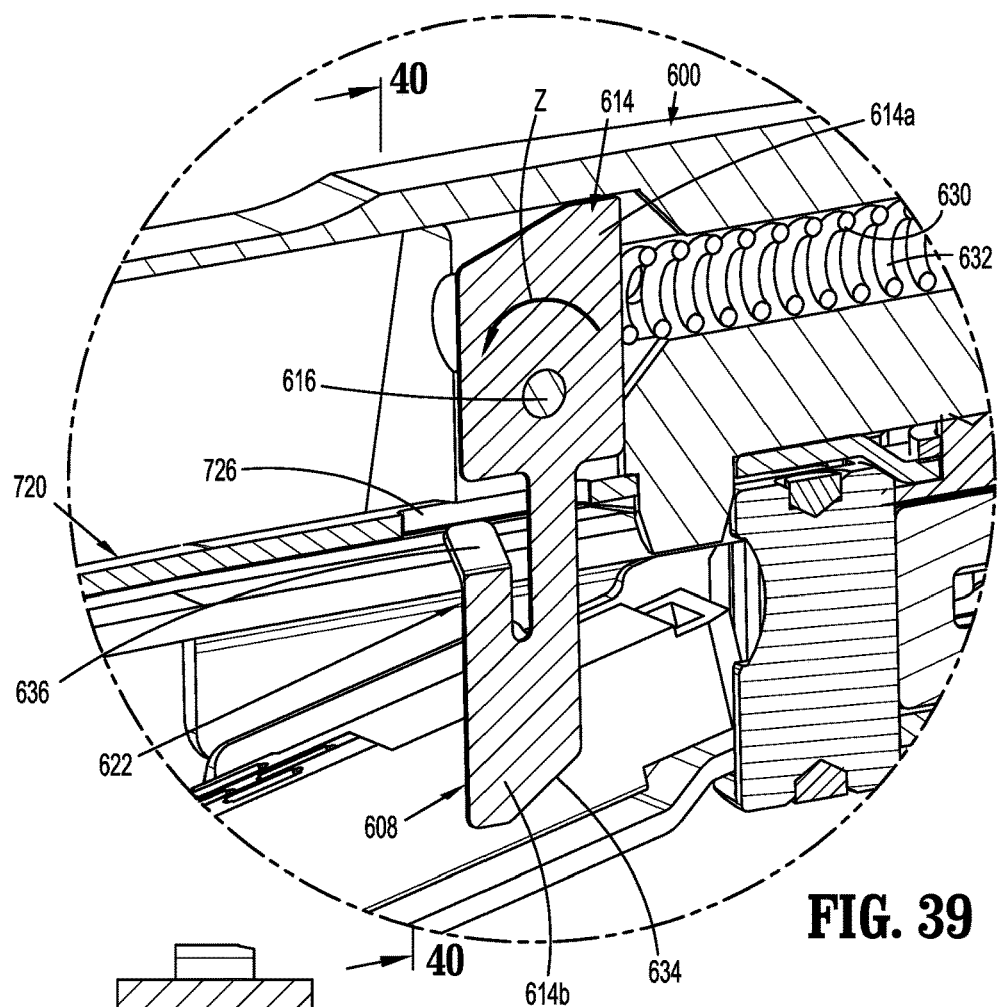
FIG. 39 is an enlarged view of the indicated area of detail shown in FIG. 38 illustrating the reload without an actuation sled.
Figure 40:
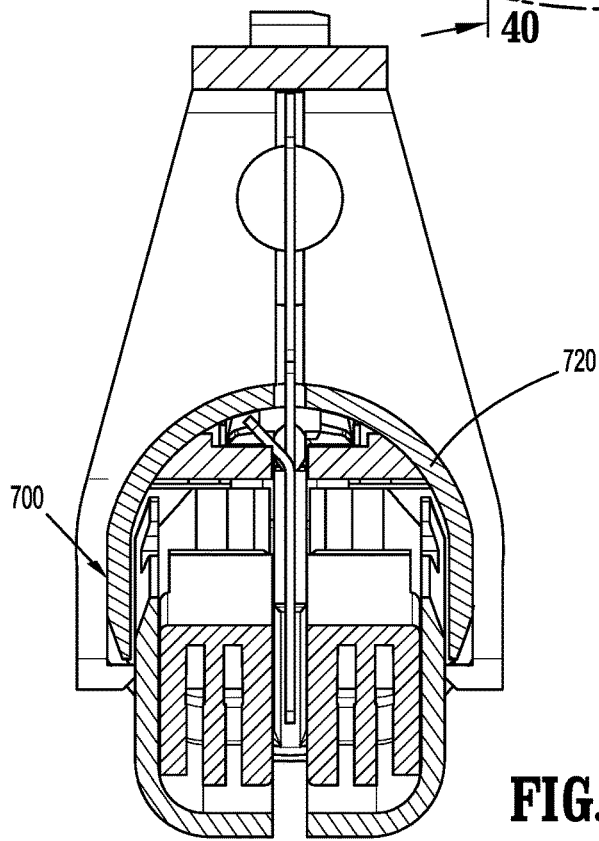
FIG. 40 is a cross-sectional view taken along section line 40-40 of FIG. 39.

FIGS. 38-40 illustrate the shipping wedge 600 attached to a staple reload 700 that is missing an actuation sled 702 (FIG. 41). When the shipping wedge 600 is secured to the staple reload 700, the detection member 608 is inserted through the through bore 726 of the anvil 720. The engagement surface 634 on the lower portion 614b of the body 614 of the detection member 608 is positioned to engage the actuation sled 702 within the tool assembly 714 to prevent passage of the resilient finger 636 of the locking member 622 of detection member 608 into the tool assembly 714 (FIG. 27). When an actuation sled 702 is not positioned within the tool assembly 714, the locking member 622 of the detection member 608 including the resilient finger 636 passes through the through bore 726 in the anvil 720. As the resilient finger 636 passes through the through bore 726, the resilient finger 636 engages walls defining the through bore 726 and is deformed, or straightened, as resilient finger passes through the through bore 726. When the resilient finger 636 passes through the through bore 726 the resilient finger will return to its non-deformed configuration extending transversely outwardly of the lower body portion 614b of the detection member 608 (FIG. 40) to passage of the resilient finger 636 through the through bore 726, to prevent removal of the locking member 622, and thus the shipping wedge 600, from the tool assembly 714. This effectively disables the staple reload 700 when an actuation sled 702 (FIG. 41) is not present in the tool assembly 714.

Figure 42:
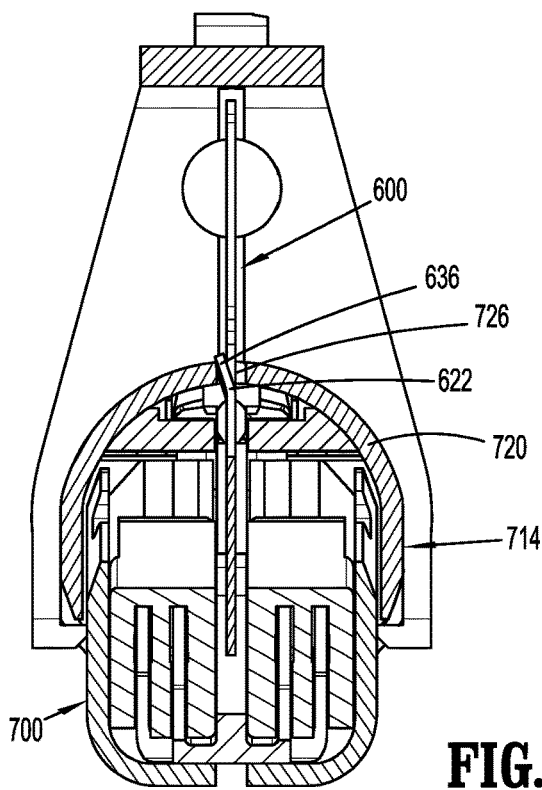
FIG. 42 is a cross-sectional view taken along section line 42-42 of FIG. 41.

FIGS. 41 and 42 illustrate the shipping wedge 600 attached to a staple reload 700 including a tool assembly 714 that has an actuation sled 702. When the shipping wedge 600 is attached to the staple reload 600, the engagement surface 634 on lower portion 614b of the body 614 of the detection member 608 engages the actuation sled 54. This engagement causes the detection member 608 to pivot in the direction of arrow "X" against the bias of the biasing member 632 to prevent the resilient finger 636 of the locking member 622 from passing through the through bore 726 of the tool assembly 714. As such, the locking member 622 can be removed from the tool assembly 714 through the through bore 726 to allow the shipping wedge 600 to be removed from the staple reload 700.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising;
   a tool assembly and a body portion, the tool assembly extending from the body portion and including an anvil and a cartridge assembly coupled to the anvil such that the tool assembly is movable between an open position and a clamped position, the anvil defining a through bore, the body portion supporting a drive assembly including a knife bar, the cartridge assembly including a staple cartridge configured to receive an actuation sled; and
   a shipping wedge releasably coupled to the stapling device, the shipping wedge including a body portion and a detection member supported on the body portion of the shipping wedge, the detection member movable from a second position to a first position and including a locking member having a locking surface, the detection member being positioned to extend through the through bore of the anvil and into the tool assembly into engagement with the actuation sled as the shipping wedge is coupled to the stapling device when the actuation sled is present in the staple cartridge, wherein in the first position of the detection member, the locking surface of the locking member does not pass through the through bore of the anvil as the shipping wedge is coupled to the stapling device, and in the second position of the detection member, the locking surface of the locking member is configured to pass through the through bore of the anvil as the shipping wedge is coupled to the stapling device to lock the shipping wedge onto the stapling device, wherein the detection member is positioned to engage the actuation sled when the actuation sled is present in the staple cartridge during coupling of the shipping wedge to the stapling device to move the detection member from the second position to the first position.

2. The surgical stapling device of claim 1, wherein the detection member is supported on a resilient arm, the resilient arm extending from the body portion of the shipping wedge.

3. The surgical stapling device of claim 2, wherein the locking surface of the locking member includes a stepped shoulder formed on the detection member.

4. The surgical stapling device of claim 3, wherein the detection member includes a cam surface, the stepped shoulder positioned along the cam surface.

5. The surgical stapling device of claim 4, wherein the cam surface is positioned to engage a portion of the anvil defining the through bore to resiliently deform the detection member such that when the locking member passes through the through bore, the stepped shoulder snaps into engagement with the portion of the anvil defining the through bore to lock the shipping wedge onto the anvil.

6. The surgical stapling device of claim 1, wherein engagement between the detection member and the actuation sled deforms the resilient arm to prevent entry of the locking member into the tool assembly.

7. The surgical stapling device of claim 1, wherein the detection member is coupled to the body portion of the shipping wedge by a pivot member.

8. The surgical stapling device of claim 7, wherein the detection member includes an upper body portion and a lower body portion, the lower body portion supporting the locking member.

9. The surgical stapling device of claim 8, wherein the locking member includes a resilient finger that extends towards the upper body portion and transversely outwardly from the lower body portion of the locking member.

10. The surgical stapling device of claim 9, wherein the lower body portion of the detection member includes an engagement surface that is positioned to engage the actuation sled when the shipping wedge is attached to the tool assembly, the engagement surface angled towards the upper body portion in a proximal direction.

11. A shipping wedge comprising:
a body portion and a detection member supported on the body portion, the detection member movable from a second position to a first position and including a locking member having a locking surface, the detection member being positioned to extend through a bore of a tool assembly into engagement with an inner component of the tool assembly when the shipping wedge is coupled to the tool assembly and the inner component is present within the tool assembly, wherein in the first position, the locking surface of the locking member is not positioned to pass through the through bore of the tool assembly when the shipping wedge is coupled to the tool assembly, and in the second position, the locking surface of the locking member is positioned to pass through the through bore of the tool assembly when the shipping wedge is coupled to the tool assembly to lock the shipping wedge onto the tool assembly, wherein the detection member is positioned to engage the inner component of the tool assembly during coupling of the shipping wedge to the tool assembly when the inner component is present in the tool assembly to move the detection member from the second position to the first position.

12. The shipping wedge of claim 11, wherein the detection member is supported on a resilient arm, the resilient arm extending from the body portion of the shipping wedge.

13. The shipping wedge of claim 12, wherein the locking surface of the locking member includes a stepped shoulder formed on the detection member.

14. The shipping wedge of claim 13, wherein the detection member includes a cam surface, the stepped shoulder positioned along the cam surface.

15. The shipping wedge of claim 14, wherein the cam surface is positioned to engage a portion of the tool assembly defining the through bore to resiliently deform the detection member such that when the locking member passes through the through bore, the stepped shoulder snaps into engagement with the portion of the tool assembly defining the through bore to lock the shipping wedge onto the tool assembly.

16. The shipping wedge of claim 15, wherein engagement between the detection member and the inner component deforms the resilient arm to prevent entry of the locking member into the tool assembly.

17. The shipping wedge of claim 11, wherein the detection member is coupled to the body portion of the shipping wedge by a pivot member.

18. The shipping wedge of claim 17, wherein the detection member includes an upper body portion and a lower body portion, the lower body portion supporting the locking member.

19. The shipping wedge of claim 18, wherein the locking member includes a resilient finger that extends from the lower body portion towards the upper body portion and transversely outwardly from the lower body portion of the locking member.

20. The shipping wedge of claim 19, wherein the lower body portion of the detection member includes an engagement surface that is positioned to engage the inner component when the shipping wedge is attached to the tool assembly, the engagement surface angled towards the upper body portion in a proximal direction.

21. A surgical stapling device comprising;
a tool assembly and a body portion, the tool assembly extending from the body portion and including an anvil and a cartridge assembly coupled to the anvil such that the tool assembly is movable between an open position and a clamped position, the anvil defining a through bore, the body portion supporting a drive assembly including a knife bar, the cartridge assembly including a staple cartridge configured to receive an actuation sled; and
a shipping wedge releasably coupled to the stapling device, the shipping wedge including a body portion and a detection member supported on the body portion of the shipping wedge, the detection member movable from a second position to a first position and including a locking member having a locking surface, the detection member configured to engage and detect a presence of the actuation sled when the actuation sled is present in the cartridge assembly and detect an absence of the actuation sled when the actuation sled is not present in the cartridge assembly, wherein the presence of the actuation sled forces the detecting member to move from the second position to the first position when the shipping wedge is coupled to the cartridge assembly, and the absence of the actuation sled allows the detection member to remain in the first position, wherein when the shipping wedge is coupled to the cartridge assembly and is in the first position, the locking surface of the detection member prevents movement of the detection member from the second position to the first position.

* * * * *